United States Patent
Quincy, III et al.

(10) Patent No.: US 6,509,284 B1
(45) Date of Patent: Jan. 21, 2003

(54) LAYER MATERIALS TREATED WITH SURFACANT-MODIFIED CHELATING AGENTS

(75) Inventors: Roger Bradshaw Quincy, III, Cumming, GA (US); Garry Roland Woltman, Greenville, WI (US); Yuelong Liu, Alpharetta, GA (US); Patricia Hsiaoyin Hwang, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/472,632

(22) Filed: Dec. 28, 1999

Related U.S. Application Data

(60) Provisional application No. 60/121,933, filed on Feb. 26, 1999.

(51) Int. Cl.$^7$ .......................... B32B 27/04; B32B 27/02
(52) U.S. Cl. .................. 442/118; 442/119; 442/121; 442/170; 442/171
(58) Field of Search ............................. 442/118, 119, 442/121, 170, 171

(56) References Cited

U.S. PATENT DOCUMENTS

| | | | |
|---|---|---|---|
| 3,338,992 A | 8/1967 | Kinney | 264/24 |
| 3,341,394 A | 9/1967 | Kinney | 161/72 |
| 3,485,706 A | 12/1969 | Evans | 161/72 |
| 3,502,538 A | 3/1970 | Petersen | 161/150 |
| 3,502,763 A | 3/1970 | Hartmann | 264/210 |
| 3,534,075 A | 10/1970 | Andress, Jr. | 260/404.5 |
| 3,542,615 A | 11/1970 | Dobo et al. | 156/181 |
| 3,692,618 A | 9/1972 | Dorschner et al. | 161/72 |
| 3,802,817 A | 4/1974 | Matsuki et al. | 425/66 |
| 3,849,241 A | 11/1974 | Butin et al. | 161/169 |
| 3,855,046 A | 12/1974 | Hansen et al. | 161/150 |
| 3,901,236 A | 8/1975 | Assarsson et al. | 128/284 |
| 3,903,259 A | 9/1975 | Hart | 424/76 |
| 3,920,020 A | 11/1975 | Kraskin | 128/290 |
| 4,015,050 A * | 3/1977 | Birchall et al. | 428/480 |
| 4,076,663 A | 2/1978 | Masuda et al. | 260/17.4 GC |
| 4,100,324 A | 7/1978 | Anderson et al. | 428/288 |
| 4,273,786 A | 6/1981 | Kraskin | 424/319 |
| 4,286,082 A | 8/1981 | Tsubakimoto et al. | 526/240 |
| 4,300,561 A | 11/1981 | Kaczmarzyk et al. | 128/285 |

(List continued on next page.)

FOREIGN PATENT DOCUMENTS

| | | | |
|---|---|---|---|
| EP | 392 607 | 10/1990 | C11D/17/04 |
| EP | 392 608 | 10/1990 | C08B/37/16 |
| EP | 0 510 619 A1 | 4/1992 | A61F/13/15 |

(List continued on next page.)

OTHER PUBLICATIONS

Dharmawardana, Udeni R., et al.: A Surface Tension Method for Determining Binding Constants for Cyclodextrin Inclusion Complexes of Ionic Surfactants, *Langmuir*, vol. 9, No. 9, 2258–2263, 1993.

I. Denter et al.: Verfahrenstechnische Methoden zur permanenten Fixierung von Cyclodextrinderivaten auf textilen Oberflächen, *Textilveredlung*, 33–39, vol. 32, No. 1/2, 1997.

*Primary Examiner*—Elizabeth M. Cole
*Assistant Examiner*—Jeremy R Pierce
(74) *Attorney, Agent, or Firm*—Pauley Petersen Kinne & Erickson

(57) ABSTRACT

A thermoplastic layer material has at least one odor-reducing surface which is wettable to aqueous liquids and capable of controlling a wide variety of malodors. The thermoplastic layer material is treated with a surfactant-modified chelating agent prepared by mixing or chemically reacting an odor-control chelating agent with a surfactant-producing compound. The layer material thus treated can be used in a wide variety of personal care and medical absorbent products, as well as other applications.

34 Claims, 5 Drawing Sheets

U.S. PATENT DOCUMENTS

| | | | |
|---|---|---|---|
| 4,340,563 A | | 7/1982 | Appel et al. .................. 264/518 |
| 4,356,190 A | | 10/1982 | Kraskin ....................... 424/319 |
| 4,377,167 A | | 3/1983 | Kaczmarzyk et al. ....... 128/285 |
| 4,425,130 A | * | 1/1984 | DesMarais .................. 604/389 |
| 4,617,230 A | | 10/1986 | Shah et al. .................. 428/288 |
| 4,638,058 A | | 1/1987 | Brandt et al. ............... 536/103 |
| 4,818,464 A | | 4/1989 | Lau ............................ 264/510 |
| 4,929,378 A | * | 5/1990 | Morita et al. ................ 252/105 |
| 5,108,820 A | | 4/1992 | Kaneko et al. .............. 428/198 |
| 5,161,686 A | * | 11/1992 | Weber et al. ................ 206/440 |
| 5,161,868 A | | 11/1992 | Weber et at. ................ 206/440 |
| 5,336,552 A | | 8/1994 | Strack et al. ................ 428/224 |
| 5,348,667 A | | 9/1994 | Bacon et al. ................. 252/8.6 |
| 5,382,400 A | | 1/1995 | Pike et al. ................... 264/168 |
| 5,429,628 A | | 7/1995 | Trinh et al. .................. 604/359 |
| 5,445,747 A | * | 8/1995 | Kvietok et al. ............... 252/86 |
| 5,533,990 A | | 7/1996 | Yeo ............................. 604/363 |
| 5,534,165 A | | 7/1996 | Pilosof et al. .............. 252/8.91 |
| 5,571,782 A | | 11/1996 | Trinh et al. ..................... 512/4 |
| 5,578,563 A | | 11/1996 | Trinh et al. ................. 510/513 |
| 5,591,146 A | | 1/1997 | Hasse ......................... 604/359 |
| 5,593,670 A | | 1/1997 | Trinh et al. ................. 424/76.1 |
| 5,594,125 A | | 1/1997 | Seyschab et al. ........... 536/103 |
| 5,648,067 A | | 7/1997 | Dillenburg et al. ........... 424/65 |
| 5,663,134 A | | 9/1997 | Trinh et al. ................. 510/406 |
| 5,668,097 A | | 9/1997 | Trinh et al. ................. 510/293 |
| 5,670,475 A | | 9/1997 | Trinh et al. ................. 510/470 |
| 5,685,872 A | | 11/1997 | Syverson | 
| 5,690,919 A | | 11/1997 | Röckl et al. .................. 424/65 |
| 5,698,476 A | | 12/1997 | Johnson et al. ............. 442/121 |
| 5,714,137 A | | 2/1998 | Trinh et al. ................. 424/76.4 |
| 5,714,445 A | | 2/1998 | Trinh et al. ................. 510/103 |
| 5,718,887 A | | 2/1998 | Wolf et al. .................... 424/65 |
| 5,733,272 A | | 3/1998 | Brunner et al. ............. 604/359 |
| 5,738,860 A | | 4/1998 | Schonfeldt et al. ......... 424/402 |
| H1732 H | | 6/1998 | Johnson ....................... 428/68 |
| 5,769,833 A | | 6/1998 | Hasse ......................... 604/359 |
| 5,780,020 A | | 7/1998 | Peterson et al. ............. 424/65 |
| 5,785,697 A | | 7/1998 | Trombetta et al. .......... 604/378 |
| 5,821,215 A | | 10/1998 | Crudden et al. ............ 510/392 |
| 5,849,325 A | | 12/1998 | Heinecke et al. ........... 424/443 |
| 5,860,959 A | | 1/1999 | Gent ........................... 604/359 |
| 5,865,792 A | | 2/1999 | Ledger et al. ................. 604/20 |
| 5,871,718 A | | 2/1999 | Lucas et al. .................. 424/65 |
| 5,871,719 A | | 2/1999 | Lucas et al. .................. 424/65 |
| 5,874,067 A | | 2/1999 | Lucas et al. .................. 424/65 |
| 5,928,631 A | | 7/1999 | Lucas et al. .................. 424/65 |
| 5,932,495 A | * | 8/1999 | Boney et al. ................ 442/121 |
| 5,942,217 A | | 8/1999 | Woo et al. .................. 424/76.1 |
| 5,955,093 A | | 9/1999 | Woo et al. .................. 424/401 |
| 5,968,404 A | | 10/1999 | Trinh et al. ................. 252/8.91 |
| 5,997,759 A | | 12/1999 | Trinh et al. ................. 252/8.91 |
| 6,001,343 A | | 12/1999 | Trinh et al. ................. 424/76.4 |
| 6,021,822 A | | 2/2000 | Iawa et al. ................... 141/110 |
| 6,028,016 A | * | 2/2000 | Yahiaoui et al. ............. 442/118 |
| 6,031,147 A | | 2/2000 | Gross ......................... 604/359 |
| 6,033,486 A | | 3/2000 | Andros .......................... 134/6 |
| 6,033,679 A | | 3/2000 | Woo et al. .................. 424/401 |
| 6,066,673 A | | 5/2000 | McIver et al. .............. 514/634 |
| 6,100,233 A | | 8/2000 | Sivik et al. .................. 512/26 |
| 6,106,738 A | | 8/2000 | Woo et al. .................. 252/8.91 |
| 6,229,062 B1 | | 5/2001 | Mandell et al. ............. 604/367 |
| 6,296,936 B1 | * | 10/2001 | Yahiaoui et al. ............. 428/378 |

FOREIGN PATENT DOCUMENTS

| | | | | |
|---|---|---|---|---|
| EP | | 510 619 | 10/1992 | ........... A61F/13/15 |
| EP | | 0 562 620 A1 | 3/1993 | ........... A61L/15/46 |
| EP | | 0 562 620 | 9/1993 | ........... A61L/15/46 |
| EP | | 562 620 | 9/1993 | ........... A61L/15/46 |
| EP | | 685 213 | 12/1995 | ........... A61F/13/15 |
| EP | | 0 894 502 A1 | 7/1997 | ........... A61K/15/18 |
| EP | | 811 390 | 12/1997 | ........... A61L/15/46 |
| EP | | 811 391 | 12/1997 | ........... A61L/15/46 |
| EP | | 813 848 | 12/1997 | ........... A61F/13/15 |
| GB | | 1 517 042 | 7/1978 | ............. A61K/7/48 |
| WO | | 94 22500 | 10/1994 | ........... A61L/15/46 |
| WO | | WO 95/17175 | 6/1995 | ............. A61K/9/70 |
| WO | | 96 04937 | 2/1996 | ............. A61L/9/01 |
| WO | | 96 05358 | 2/1996 | .......... D06M/15/11 |
| WO | | 96/24318 | 8/1996 | ........... A61F/13/15 |
| WO | | WO 97/31698 | 9/1997 | ........... B01D/53/04 |
| WO | | 98 07455 | 2/1998 | ............. A61L/9/01 |
| WO | | 98 17239 | 4/1998 | ............. A61K/7/32 |
| WO | | 98 17240 | 4/1998 | ............. A61K/7/32 |
| WO | | 98 18439 | 5/1998 | ............. A61K/7/32 |
| WO | | WO 98/20916 | 5/1998 | ........... A61L/15/46 |
| WO | | 98 26808 | 6/1998 | ............. A61L/9/01 |
| WO | | WO 98/56342 | 12/1998 | ............. A61K/7/48 |
| WO | | 99/45973 | 9/1999 | ........... A61L/15/44 |
| WO | | 99/45974 | 9/1999 | ........... A61L/15/44 |
| WO | | 00/10500 | 3/2000 | ........... A61F/13/15 |

* cited by examiner

LAYER MATERIALS TREATED WITH SURFACANT-MODIFIED CHELATING AGENTS

This application claims the benefit of provisional application No. 60/121,933, filed Feb. 26, 1999.

FIELD OF THE INVENTION

This invention relates to chemical compounds and blends which prevent or control odor and impart surface wetting properties to layer materials. In particular, the invention relates to layer materials treated with these dual purpose chemical compounds and blends.

BACKGROUND OF THE INVENTION

Nonwoven fabrics, films, foams, and other layer materials and their manufacture have been the subject of extensive development resulting in a wide variety of materials for numerous applications. For example, nonwovens of light basis weight and open structure are used in personal care items such as disposable diapers as liner fabrics that provide dry skin contact but readily transmit fluids to more absorbent materials which may also be nonwovens of a different composition and/or structure. Nonwovens of heavier weights may be designed with pore structures making them suitable for filtration, absorbent and barrier applications such as wrappers for items to be sterilized, wipers or protective garments for medical, veterinary or industrial uses. Even heavier weight nonwovens have been developed for recreational, agricultural and construction uses. Films, foams, and other layer materials are also employed in some of these applications, and may be combined with nonwoven webs.

It is not always possible to efficiently produce a layer material having all the desired properties as formed, and it is frequently necessary to treat the material with a surfactant to improve or alter surface properties such as wettability by one or more fluids, repellency to one or more fluids, electrostatic characteristics, conductivity, and softness, to name just a few examples. Conventional surface treatments involve steps such as dipping the substrate in a treatment bath, coating or spraying the substrate with the treatment composition, and printing the substrate with the treatment composition. For cost and other reasons it is usually desired to use the minimum amount of treatment composition that will produce the desired effect with an acceptable degree of uniformity.

For many thermoplastic layer material end use applications, it is desirable to reduce, prevent, or eliminate odors. For diapers and other incontinence products, it is desirable to reduce or eliminate the odor of ammonia which is present in urine. For feminine hygiene products, it is desirable to reduce or eliminate the odors of trimethylamine and triethylamine. Other common odor-producing substances include isovaleric acid, dimethyl disulfide, and dimethyl trisulfide.

Odor control agents include odor inhibitors, odor absorbers, odor adsorbers and other compounds which reduce, prevent, or eliminate odors. Odor inhibitors prevent the odor from forming. For example, U.S. Pat. No. 4,273,786 to Kraskin teaches the use of an aminopolycarboxylic acid compound for inhibiting the formation of ammonia from urea in urine. Odor absorbers and adsorbers remove odor after it is formed. Examples of odor control agents that remove odor by absorption or adsorption include activated carbon, silica, and cyclodextrin.

Typical odor control agents based on aminocarboxylic acid compounds (e.g., ethylenediaminetetraacetic acid (EDTA), salts of EDTA) and other chelating agents cannot easily be applied from aqueous solutions to thermoplastic layer substrates such as polyolefin nonwoven fabrics, films, and foam layers because the surface tension of these solutions is too high to wet out the hydrophobic substrate. Personal care products such as diapers and feminine care pads typically contain polyolefin nonwoven fabrics and/or other thermoplastic cover layers. Therefore, typical odor control agents cannot usually be applied to the thermoplastic layer components of personal care products. Instead, these odor control agents are usually introduced as powders to the product, which has several drawbacks. For example, placement and containment of the powder in the product can be troublesome. More importantly, powders do not present optimum surface area for odor absorption due to a rather low surface to volume ratio. Therefore, more odor control agent will be needed if in powder form.

There is a need or desire for odor-preventing and odor-absorbing compounds and blends which can be applied to a hydrophobic (e.g., thermoplastic) layer substrate in a liquid or solvent form, and which have enough surface wetting properties to facilitate uniform fluid distribution and durability.

SUMMARY OF THE INVENTION

The present invention is directed to a thermoplastic layer material which has been treated with a surfactant-modified odor control agent. The surfactant-modified odor control agent can be prepared by blending an odor control chelating agent with a surfactant, or by chemically reacting an odor control chelating agent with a surfactant-producing compound. Surfactant-producing compounds include surfactants, and other compounds which behave as surfactants following the chemical reaction. The surfactant-modified odor control agent can be applied to the thermoplastic layer material using conventional internal or external application techniques for surfactants, and is preferably applied using an external application technique. The resulting treated substrate is more wettable to aqueous liquids, and prevents, reduces and/or absorbs odors at its surfaces.

The thermoplastic layer material can be a hydrophobic material, made using one or more thermoplastic polymers. The layer material may be porous and water-permeable. For instance, the layer material may be a thermoplastic nonwoven filament web, a thermoplastic film, a foam layer, or a combination thereof. A thermoplastic nonwoven filament web is preferred. The treated thermoplastic layer material can be used in a wide variety of personal care products and medical products, and in other applications.

The surfactant-modified odor control agents can be applied to hydrophobic substrates (for example, polyolefin-based films, foam layers, and nonwoven webs) from an aqueous solution, because the surface tension of the solution is low enough to wet out the low surface energy substrate. For instance, the coating of the surfactant-modified odor control agent on the polyolefin fibers of a polyolefin nonwoven fabric will optimize the surface to volume ratio of odor control chemistry, and thus provide better odor control (e.g., odor absorption, adsorption, prevention or inhibition). Furthermore, fibers coated with a surfactant-modified odor control agent will be in direct contact with body fluids as the fluids enter and wick through the fabric components of the personal care product. This will provide optimum odor control since the odors are believed to emanate from the body fluids.

It is thus a feature and advantage of the invention to provide a treated thermoplastic layer material having at least one surface which is more wettable to aqueous liquids than the untreated layer material, and which inhibits and/or absorbs common odors.

It is also a feature and advantage of the invention to provide a personal care fabric or product which utilizes the treated thermoplastic layer material that is more wettable, and inhibits and/or absorbs odors on at least one outer surface.

It is also a feature and advantage of the invention to provide a medical fabric or product which utilizes the treated thermoplastic layer material that is more wettable, and inhibits and/or absorbs odors on at least one outer surface.

DEFINITIONS

The term "layer material" refers to a material that exists in the form of a flexible, fabric-like or paper-like material, including without limitation nonwoven filament webs and fabrics, thermoplastic films, flexible thermoplastic foam materials, and multilayer combinations including one or more of these.

The term "water-permeable porous layer material" refers to a material present in one or more layers, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material.

The term "nonwoven fabric or web" means a web having a structure of individual fibers or threads which are interlaid, but not in a regular or identifiable manner as in a knitted fabric. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91.)

The term "microfibers" means small diameter fibers having an average diameter not greater than about 75 microns, for example, having an average diameter of from about 1 micron to about 50 microns, or more particularly, microfibers may have an average diameter of from about 1 micron to about 30 microns. Another frequently used expression of fiber diameter is denier, which is defined as grams per 9000 meters of a fiber. For a fiber having circular cross-section, denier may be calculated as fiber diameter in microns squared, multiplied by the density in grams/cc, multiplied by 0.00707. A lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 ($15^2 \times 0.89 \times 0.00707 = 1.415$). Outside the United States the unit of measurement is more commonly the "tex," which is defined as the grams per kilometer of fiber. Tex may be calculated as denier/9.

The term "spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pats. No. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average diameters larger than about 7 microns, more particularly, between about 10 and 30 microns.

The term "meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than 10 microns in diameter, and are generally self bonding when deposited onto a collecting surface. Meltblown fibers used in the present invention are preferably substantially continuous in length.

The term "monocomponent" fiber refers to a fiber formed from one or more extruders using only one polymer. This is not meant to exclude fibers formed from one polymer to which small amounts of additives have been added for color, anti-static properties, lubrication, hydrophilicity, repellency, etc. These additives, e.g., titanium dioxide for color, are generally present in an amount less than 5 weight percent and more typically about 2 weight percent or less.

The term "coform" material refers to a product containing about 10–90% by weight of thermoplastic meltblown fibers and about 10–90% by weight of staple-length pulp fibers dispersed within the meltblown fiber matrix. More commonly, coform materials contain about 20–70% by weight thermoplastic meltblown fibers and about 30–80% by weight pulp fibers.

The term "film" refers to a thermoplastic film made using a film extrusion process, such as a cast film or blown film extrusion process. The term "water-permeable porous films" refers to films rendered porous by puncturing or aperturing, and to films rendered porous by mixing polymer with filler, forming a film from the mixture, and stretching the film.

The term "foam material" refers to a thermoplastic layer material made with the aid of a foaming process. The term "open-celled foam material" refers to a foam layer whose cells interconnect, or otherwise create pores from one surface of the layer to the opposite surface.

The term "polymer" includes, but is not limited to, homopolymers, copolymers, such as for example, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to isotactic, syndiotactic and atactic symmetries.

The term "bicomponent filaments or fibers" refers to fibers which have been formed from at least two polymers extruded from separate extruders but spun together to form one fiber. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another or may be a side-by-side arrangement or an "islands-in-the-sea" arrangement. Bicomponent fibers are taught in U.S. Pat. No. 5,108,820 to Kaneko et al., U.S. Pat. No. 5,336,552 to Strack et al., and U.S. Pat. No. 5,382,400 to Pike et al., each of which is incorporated herein in its entirety by reference. For two component fibers, the polymers may be present in ratios of 75/25, 50/50, 25/75 or any other desired ratios. Conventional additives, such as pigments and surfactants, may be incorporated into one or both polymer streams, or applied to the filament surfaces.

The term "pulp fibers" refers to fibers from natural sources such as woody and non-woody plants. Woody plants include, for example, deciduous and coniferous trees. Non-woody plants include, for instance, cotton, flax, esparto grass, milkweed, straw, jute hemp, and bagasse.

The term "average pulp fiber length" refers to a weighted average length of pulp determined using a Kajaani fiber analyzer Model No. FS-100 available from Kajaani Oy Electronics in Kajaani, Finland. Under the test procedure, a fiber sample is treated with a macerating liquid to ensure that no fiber bundles or shives are present. Each fiber sample is dispersed in hot water and diluted to about a 0.001% concentration. Individual test samples are drawn in approximately 50 to 500 ml portions from the dilute solution and tested using the standard Kajaani fiber analysis procedure. The weighted average fiber lengths may be expressed by the following equation:

$$\sum_{X_i > 0}^{k} (X_i * n_i)/n$$

where k=maximum fiber length, $X_i$=individual fiber length, $n_i$=number of fibers having length $X_i$ and n=total number of fibers measured.

The term "superabsorbent material" refers to a water-swellable, water-insoluble organic or inorganic material capable, under the most favorable conditions, of absorbing at least about 20 times its weight, preferably at least about 30 times its weight in an aqueous solution containing 0.9% by weight sodium chloride.

The term "through-air bonding" or "TAB" means a process of bonding a nonwoven, for example, a bicomponent fiber web in which air which is sufficiently hot to melt one of the polymers of which the fibers of the web are made is forced through the web. The air velocity is often between 100 and 500 feet per minute and the dwell time may be as long as 6 seconds. The melting and resolidification of the polymer provides the bonding. Through-air bonding has restricted variability and is generally regarded as a second step bonding process. Since TAB requires the melting of at least one component to accomplish bonding, it is restricted to webs with two components such as bicomponent fiber webs or webs containing an adhesive fiber or powder.

The term "thermal point bonding" involves passing a fabric or web of fibers to be bonded between a heated calender roll and an anvil roll. The calender roll is usually, though not always, patterned in some way so that the entire fabric is not bonded across its entire surface. As a result, various patterns for calender rolls have been developed for functional as well as aesthetic reasons. One example of a pattern has points and is the Hansen Pennings or "H&P" pattern with about a 30% bond area with about 200 bonds/square inch as taught in U.S. Pat. No. 3,855,046 to Hansen and Pennings. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5%. Another typical point bonding pattern is the expanded Hansen and Pennings or "EHP" bond pattern which produces a 15% bond area with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15%. Yet another common pattern is the C-Star pattern which has a bond area of about 16.9%. The C-Star pattern has a cross- directional bar or "corduroy" design interrupted by shooting stars. Other common patterns include a diamond pattern with repeating and slightly offset diamonds and a wire weave pattern looking as the name suggests, e.g., like a window screen. Typically, the percent bonding area varies from around 10% to around 30% of the area of the fabric laminate web. As is well known in the art, the spot bonding holds the laminate layers together as well as imparts integrity to each individual layer by bonding filaments and/or fibers within each layer.

The term "personal care product" includes without limitation diapers, training pants, swim wear, absorbent underpants, baby wipes, adult incontinence products, and feminine hygiene products.

The term "medical product" includes without limitation garments, underpads, bandages, absorbent drapes, and medical wipes.

The term "hydrophilic" or "wettable" means that the polymeric material has an apparent surface free energy such that the polymeric material is wettable by an aqueous medium, i.e., a liquid medium of which water is a major component. That is, an aqueous medium wets the nonwoven fabric. "Apparent surface free energy" refers to the highest surface tension of an aqueous liquid which wets the polymeric material. For example, the apparent surface free energy of a polymeric material that is wetted by an aqueous liquid having a surface tension of 72 dynes/cm, is at least 72 dynes/cm and possibly higher. In the fabrics of the invention, a surface of the nonwoven fabric has been treated with a surfactant-modified odor control agent using internal or external application techniques as described below.

The term "surfactant" refers to a compound or blend which, when applied to a surface of a substrate, causes the surface to become more "wettable" as defined above. In one instance, the substrate is not independently wettable and the surfactant causes it to become wettable. In another instance, the substrate is somewhat wettable and the surfactant causes it to become more wettable, or more easily wetted.

The term "surfactant-producing moiety" or "surfactant-producing compound" refers to a chemical group or compound which, when reacted or blended with another compound (e.g., an odor control agent) causes the reacted compound or blend to behave as a surfactant. The surfactant-producing moiety or compound may or may not behave as a surfactant prior to the chemical reaction or blending.

The term "odor control agent" includes compounds and blends which inhibit the formation of at least one undesirable odor, as well as compounds and blends which absorb an undesirable odor that has already formed.

The term "surfactant-modified odor control agent" refers to a blend, and/or a reaction product, between an odor control agent and a surfactant or surfactant-producing compound, which acts as both a surfactant and an odor control agent.

DETAILED DESCRIPTION OF THE PRESENTLY PREFERRED EMBODIMENTS

Figure 1:
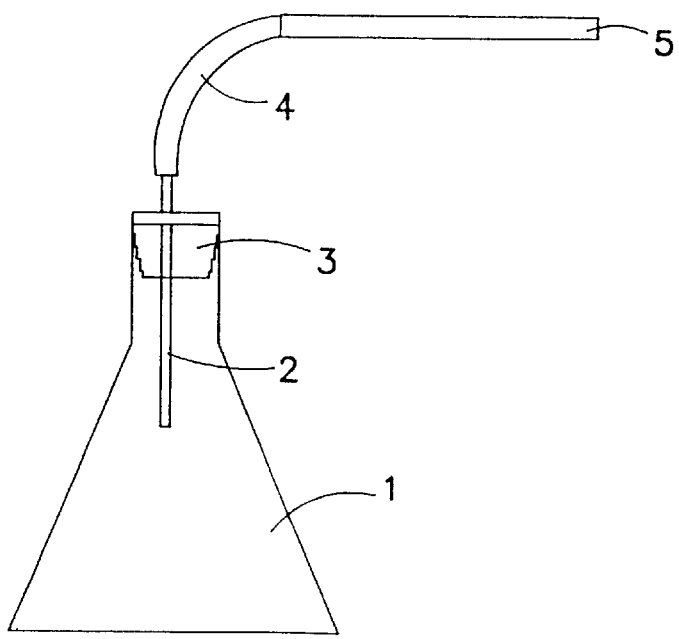
FIG. 1 illustrates testing apparatus used in Examples 1–6.

The present invention is a layer material having at least one odor-reducing surface. The starting material for the invention is a thermoplastic layer material. Examples of suitable starting materials include thermoplastic nonwoven filament webs, thermoplastic films, and thermoplastic foam layers. The starting material may be a porous, water-permeable layer material. Examples of water-permeable layer materials include thermoplastic nonwoven filament webs, open-celled foam layers, and films which are apertured or otherwise rendered porous, such as by stretching a film made from a mixture of a thermoplastic material and a particulate filler.

The starting material is treated with a surfactant-modified odor control agent. The surfactant-modified odor control agent is produced by blending an odor control chelating agent with a surfactant compound, or by chemically reacting an odor control chelating agent with a surfactant-producing compound. The term "surfactant-producing compound" refers to surfactants, and to other compounds which function as surfactants following the chemical reaction. The surfactant-modified odor control agent is applied to the starting material using conventional techniques for applying surfactants externally or internally. Preferably, the surfactant-modified odor control agent is applied externally in the form of a liquid, using techniques such as dipping, spraying, brushing, or other liquid coating techniques. The surfactant-modified odor control agent may be blended with water or another solvent to facilitate its application.

The preferred layer material for the invention is a nonwoven web including a plurality of filaments made from one or more polymers. The nonwoven web may be a spunbond web, a meltblown web, a bonded carded web, or another type of nonwoven web, and may be present in a single layer or a multilayer composite including one or more nonwoven web layers and, in some instances, one or more film or foam layers. The web may include monocomponent or bicomponent filaments, or a combination including one or both filament types. The nonwoven web may have a variety of basis weights, preferably ranging from about 0.1–200 grams per square meter (gsm). One preferred nonwoven web is a coform material, which includes a matrix of polyolefin meltblown fibers and a large percentage (often 30–80% by weight) of pulp fibers dispersed in the matrix of meltblown fibers. Another preferred nonwoven web is an airlaid web of polyolefin fibers and pulp fibers.

A wide variety of thermoplastic polymers may be used to construct the starting thermoplastic layer material, including without limitation polyamides, polyesters, polyolefins, copolymers of ethylene and propylene, copolymers of ethylene or propylene with a $C_4$–$C_{20}$ alpha-olefin, terpolymers of ethylene with propylene and a $C_4$–$C_{20}$ alpha-olefin, ethylene vinyl acetate copolymers, propylene vinyl acetate copolymers, styrene-poly(ethylene-alpha-olefin) elastomers, polyurethanes, A-B block copolymers where A is formed of poly(vinyl arene) moieties such as polystyrene and B is an elastomeric midblock such as a conjugated diene or lower alkene, polyethers, polyether esters, polyacrylates, ethylene alkyl acrylates, polyisobutylene, poly-1-butene, copolymers of poly-1-butene including ethylene-1-butene copolymers, polybutadiene, isobutylene-isoprene copolymers, and combinations of any of the foregoing. Polyolefins are preferred. Polyethylene and polypropylene homopolymers and copolymers are most preferred.

The odor control agent, which can be mixed or chemically reacted with a surfactant to make the surfactant-modified odor control agent, includes a chelating agent. Suitable chelating agents include without limitation aminopolycarboxylic acids, their alkali metal salts, and combinations thereof. Suitable aminopolycarboxylic acids and alkali metal (preferably sodium) salts thereof, include without limitation ethylenediamine tetraacetic acid (EDTA), the alkali metal salts of EDTA (for instance, $Na_2EDTA$, $Na_3EFDTA$, and $Na_4EDTA$), nitrilotriacetic acid, the alkali metal (e.g., sodium) salts of cyclohexanediamine tetraacetic acid, diethylenetriamine pentaacetic acid (DTPA), hydroxyethylenediamine triacetic acid (HEDTA), pentasodium diethylenetriamine pentaacetate, trisodium hydroxyethyl ethylenediamine triacetate, and combinations thereof. A particularly suitable aminopolycarboxylic acid is EDTA. Suitable chelating agents also include polyamino disuccinic acids and alkali metal salts of them, including acids and salts of ethylenediamine-N,N'-disuccinic acid, diethylenetriamine-N,N"-disuccinic acid, triethylenetetraamine-N,N'"-disuccinic acid, 1,6-hexamethylenediamine N,N-disuccinic acid, tetraethylenepentaamine-N,N" "-disuccinic acid, 2-hydroxypropylene-1,3-diamine-N,N'-disuccinic acid, 1,2-propylenediamine-N,N'-disuccinic acid, 1,3-propylenediamine-N,N'-disuccinic acid, cis-cyclohexanediamine-N,N'-disuccinic acid, trans-cyclohexanediamine-N,N'-disuccinic acid, and ethylene-bis (oxyethylenenitrilo)-N,N'-disuccinic acid. The preferred polyamino disuccinic acid is ethylenediamine-N,N'-disuccinic acid. Chelating agents can act as odor inhibitors which prevent odor from occurring by interfering with reactions that produce odors, as well as odor absorbents which remove or minimize existing odor-producing compounds. When the chelating agents alone are applied to the starting substrate material, the material does not have sufficient wettability to aqueous liquids.

In accordance with the invention, the odor control agent is mixed with a surfactant, and/or chemically reacted with a surfactant-producing compound, to yield the surfactant-modified odor control agent which can serve both functions. The surfactant and/or surfactant-producing compound should include at least one functional group which is compatible with the thermoplastic polymer used to make the fibrous nonwoven web. Suitable functional groups include alkyl groups having about 3–20 carbon atoms, including without limitation propyl, benzyl, isopropyl, butyl, tertiary butyl, allyl, alkyl-benzyl, hexyl, octyl, decyl, lauryl, myristyl, palmityl, cocyl, oleyl, stearyl, and other common alkyl groups. Alkyl groups can be combined with aminopolycarboxylic acids and their salts by mixing an alkyl-containing surfactant with an odor control chelating agent based on an aminopolycarboxylic acid or salt. The mixing can occur in a solvent such as water. Alkyl groups can also be chemically reacted with aminopolycarboxylic acids and their salts by reacting a carboxyl group or salt thereof under appropriate conditions with an alkyl surfactant compound, an alkyl halide, an alkylating alkyl sulfate reactant, or another suitable alkylating compound. The mixing and/or chemical reaction can be accomplished using conventional techniques.

Other suitable functional groups include acyl groups having about 3–20 carbon atoms, including without limitation, propionyl, butyryl, trifluoroacetyl, benzoyl, caproyl, caprylyl, capryl, lauroyl, myristoyl, palmitoyl, stearoyl, cocoyl, oleoyl, and other common acyl groups. Compounds containing acyl groups can be combined with aminopolycarboxylic acids and their salts by mixing an acyl-containing surfactant with an aminocarboxylic acid (or salt)-based chelating agent. Again, a solvent such as water may be employed. Acyl groups can also be formed on aminopolycarboxylic acids and their salts by chemically reacting a compound containing carboxyl group or salt thereof with an acyl surfactant compound, acid anhydride, acid chloride, or another suitable acylating compound. Again, the mixing and/or chemical reaction may be accomplished using conventional techniques.

Other suitable functional groups include any aliphatic hydrocarbon group or derivative thereof which can be blended or reacted with an aminopolycarboxylic acid to render it surface active. Examples include certain surfactant compounds containing perfluoro and/or siloxane groups, other compounds containing these groups, and other suitable compounds.

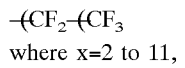
where x=2 to 11,

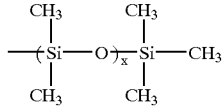
where x=2 to 20, and

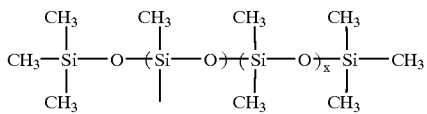
where x=2 to 20.

One particularly suitable surfactant is AHCOVEL®Base N-62, available from the Hodgson Chemical Company. This surfactant is a blend of ethoxylated hydrogenated castor oil and sorbitan monooleate. The chemical formulas for these components are as follows:

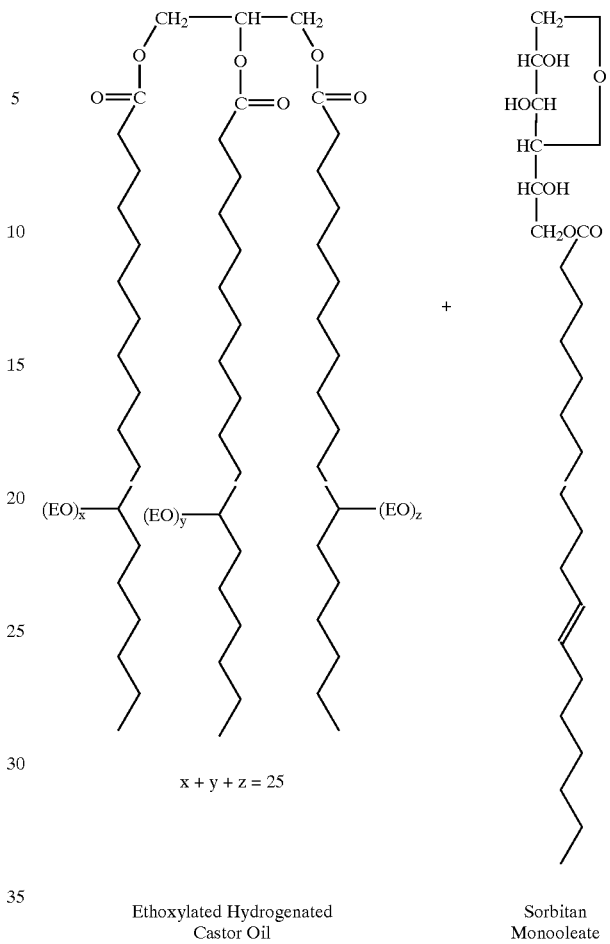

Ethoxylated Hydrogenated Castor Oil

Sorbitan Monooleate

AHCOVEL®Base N-62 can be blended or chemically reacted with a suitable odor control chelating agent, to produce a surfactant-modified odor control agent. One particularly suitable surfactant-modified odor control agent is a blend of AHCOVEL®Base N-62 with EDTA or a sodium salt of EDTA. A presently preferred blend contains about 3–10 parts (more preferably 6–8 parts) by weight EDTA (or a sodium salt thereof) per one part by weight AHCOVEL®Base N-62, in an aqueous solution containing about 90.0–99.9% water.

Another suitable surfactant is CETIOL®1414E, available from the Henkel Corporation. CETIOL®01414E is an ethoxylated ester derivative of myristic acid. One particularly suitable surfactant-modified odor control agent is a blend of CETIOL®1414E with EDTA or a sodium salt of EDTA. A presently preferred blend contains about 3–10 parts (more preferably 6–8 parts) by weight EDTA (or a sodium salt thereof) per one part by weight CETIOL®1414E in a similar aqueous solution.

Another suitable surfactant is MASIL®SF-9, available from PPG Industries, Inc. MASIL®SF-9 is an ethoxylated siloxane, and can be combined with EDTA or a sodium salt thereof, in a manner similar to that described above for AHCOVEL®Base N-62 or CETIOL®81414E.

Other useful surfactant-modified odor control agents are acyl-modified aminopolycarboxylic acids (EDTA's) and their salts. A specific acyl-modified EDTA is a mono-, di-, or tri-sodium lauroyl ethylenediamine triacetic acid salt (also referred to as $Na_xLED3A$, where x=1–3), available from Hampshire Chemical Corp. This is a hybrid reacted compound (as opposed to a blend) which serves as a surfactant-modified odor control agent. Another acyl-modified EDTA is a mono-, di- or tri-sodium capryloyl ethylenediamine triacetic acid ($Na_xC_8ED3A$, where x=1–3). This is also a hybrid reacted compound which serves as a surfactant-modified odor control agent.

The surfactant-modified odor control agent may be applied using internal or external application techniques known in the art. Some compounds and blends operate more favorably when applied internally and are called "internal additives." Others operate more favorably when applied externally and are called "external additives." Still other compounds and blends operate suitably as both internal and external additives.

As is generally known, an internal additive is typically blended with the polymer used to make the nonwoven web, film, foam, or other thermoplastic layer material, and migrates to the surfaces of the nonwoven web filaments or other layer material during and/or after their formation. Often, the migration results from a stimulus, such as heat applied to the thermoplastic material. An external additive is applied externally to the surfaces of the layer material after it is formed. An external additive may be applied by dipping, soaking, spraying, or otherwise coating the thermoplastic layer material with a solvent or other medium containing the additive.

External application methods are presently preferred for the surfactant-modified odor control agents used with the treated materials of the invention. The surfactant-modified odor control agent (whether formed by blending or chemical reaction) may be mixed with water or another suitable solvent in a concentration of about 0.1–30% by weight of the agent, preferably about 0.5–15% by weight of the agent, more preferably about 1–5% by weight of the agent. The solution may then be applied to a thermoplastic layer material by immersion, spraying, brush coating, printing, or another suitable technique. The treated layer material can then be dried using heat, forced air convection, vacuum-induced evaporation, or another conventional drying technique.

The treated layer materials thus formed have wettability to aqueous liquids, and odor resistance to a wide variety of odor-producing moieties. The terms "odor resistance" and "odor control" refer to the ability of the treated layer materials to react with, inhibit, neutralize, form complexes with, or otherwise prevent the odor-producing compounds from forming, or reduce the odors produced by them. Examples of odor-producing compounds which the treated layer materials of the invention may inhibit, reduce or eliminate, include without limitation ammonia, trimethylamine, triethylamine, isovaleric acid, dimethyldisulfide, dimethyltrisulfide, indole, skatole, and the like.

The amount of surfactant-modified odor control agent needed to provide sufficient wetting and odor absorption may vary depending on the surfactant moiety and odor control agent blended or reacted together, the base polymer type, and whether the surfactant-modified odor control agent is added internally or externally. On a solvent-free weight basis, the surfactant-modified odor control agent should generally constitute about 0.1–10% by weight of the thermoplastic layer material to which it is applied, preferably about 0.5–8% by weight, more preferably about 2–7% by weight.

The treated thermoplastic layer materials thus formed can be used in a wide variety of absorbent product applications including, in particular, personal care absorbent products. Personal care absorbent products include diapers, training pants, swim wear, absorbent underpants, baby wipes, adult incontinence products, feminine hygiene products, and the like. In absorbent products, the treated layer material (if water permeable) can be used as a cover sheet or containment matrix for an absorbent medium capable of absorbing aqueous liquids. An absorbent medium may include, for instance, pulp fibers alone or in combination with a superabsorbent material. The treated layer material can also be used in medical absorbent products, including without limitation garments, underpads, absorbent drapes, bandages, and medical wipes.

The pulp fibers may be any high-average fiber length pulp, low-average fiber length pulp, or mixtures of the same. Preferred pulp fibers include cellulose fibers. The term "high average fiber length pulp" refers to pulp that contains a relatively small amount of short fibers and non-fiber particles. High fiber length pulps typically have an average fiber length greater than about 1.5 mm, preferably about 1.5–6 mm, as determined by an optical fiber analyzer, such as the Kajaani tester referenced above. Sources generally include non-secondary (virgin) fibers as well as secondary fiber pulp which has been screened. Examples of high average fiber length pulps include bleached and unbleached virgin softwood fiber pulps.

The term "low average fiber length pulp" refers to pulp that contains a significant amount of short fibers and non-fiber particles. Low average fiber length pulps have an average fiber length less than about 1.5 mm, preferably about 0.7–1.2 mm, as determined by an optical fiber analyzer such as the Kajaani tester referenced above. Examples of low fiber length pulps include virgin hardwood pulp, as well as secondary fiber pulp from sources such as office waste, newsprint, and paperboard scrap.

Examples of high average fiber length wood pulps include those available from the U.S. Alliance Coosa Pines Corporation under the trade designations Longlac 19, Coosa River 56, and Coosa River 57. The low average fiber length pulps may include certain virgin hardwood pulp and secondary (i.e., recycled) fiber pulp from sources including newsprint, reclaimed paperboard, and office waste. Mixtures of high average fiber length and low average fiber length pulps may contain a predominance of low average fiber length pulps. For example, mixtures may contain more than about 50% by weight low-average fiber length pulp and less than about 50% by weight high-average fiber length pulp.

The term "superabsorbent" or "superabsorbent material" refers to a water swellable, water-insoluble organic or inorganic material capable, under the most favorable conditions, of absorbing at least about 20 times its weight and, more desirably, at least about 30 times its weight in an aqueous solution containing 0.9 weight percent sodium chloride.

The superabsorbent materials can be natural, synthetic and modified natural polymers and materials. In addition, the superabsorbent materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic superabsorbent material polymers include the alkali metal and ammonium salts of poly(acrylic acid) and poly(methacrylic acid), poly(acrylamides), poly (vinyl ethers), maleic anhydride copolymers with vinyl ethers and alpha-olefins, poly(vinyl pyrrolidone), poly (vinylmorpholinone), poly(vinyl alcohol), and mixtures and copolymers thereof. Further superabsorbent materials include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic superabsorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Superabsorbent materials may be xerogels which form hydrogels when wetted. The term "hydrogel," however, has commonly been used to also refer to both the wetted and unwetted forms of the superabsorbent polymer material. The superabsorbent materials can be in many forms such as flakes, powders, particulates, fibers, continuous fibers, networks, solution spun filaments and webs. The particles can be of any desired shape, for example, spiral or semi-spiral, cubic, rod-like, polyhedral, etc. Needles, flakes, fibers, and combinations may also be used.

Superabsorbents are generally available in particle sizes ranging from about 20 to about 1000 microns. Examples of commercially available particulate superabsorbents include SANWET®IM 3900 and SANWET®IM-5000P, available from Hoescht Celanese located in Portsmouth, Va., DRYTECH®2035LD available from Dow Chemical Co. located in Midland, Mich. and FAVOR®SXM880, available from Stockhausen, located in Greensboro, N.C. An example of a fibrous superabsorbent is OASIS®101, available from Technical Absorbents, located in Grimsby, United Kingdom.

As indicated above, the treated thermoplastic layer material may be a cover sheet or a matrix for an absorbent medium. Nonwoven filaments may be employed as a matrix, and may be combined with pulp fibers and (optionally) a superabsorbent material using processes well known in the art. For example, a coform process may be employed, in which at least one meltblown diehead is arranged near a chute through which other materials are added while the web is forming. Coform processes are described in U.S. Pat. No. 4,818,464 to Lau and 4,100,324 to Anderson et al., the disclosures of which are incorporated by reference. Thermoplastic nonwoven filaments and pulp fibers may also be combined using hydraulic entangling or mechanical entangling. A hydraulic entangling process is described in U.S. Pat. No. 3,485,706 to Evans, the disclosure of which is incorporated by reference.

When treated thermoplastic nonwoven filaments are used as a matrix for an absorbent nonwoven web composite, the composite should contain about 5–97% by weight pulp fibers, preferably about 35–95% by weight pulp fibers, more preferably about 50–95% by weight pulp fibers. When a superabsorbent material is present, it should constitute about 5–90% by weight of the composite, preferably about 10–60% by weight, more preferably about 20–50% by weight. In either case, the thermoplastic nonwoven filament matrix should constitute about 3–95% by weight of the composite, preferably about 5–65% by weight, more preferably about 5–50% by weight.

After combining the ingredients together, the absorbent nonwoven composites may be bonded together using the thermal point bonding or through-air bonding techniques described above, to provide a coherent high integrity structure.

EXAMPLES 1–6

(Odor Inhibition)

The following procedures were used to measure odor inhibition of ammonia generated from synthetic urine. The base fabric tested was a coform material containing 30% by weight meltblown polypropylene fibers and 70% by weight pulp fibers dispersed within the matrix of meltblown fibers. The coform material had a basis weight of 170 grams/square meter. Samples of base fabric were treated with various coatings by soaking the fabric in an aqueous solution containing the surface coatings, squeezing the excess solution from the treated fabrics, and drying the treated fabrics. The treated fabrics were cut into samples weighing 0.5 grams each.

The treated fabric samples (0.5 grams weight) were each exposed to an insult of 6 ml synthetic urine at 37° C. which had been inoculated with $5.6 \times 10^9$ colony forming units/ml of proteus mirabilis bacteria. The 6 ml quantity was selected because the fabric sample of Example 2 (described below) was able to absorb and hold that amount of the fluid. This bacteria, which is typically present on the surface of human skin, facilitates the formation of ammonia from urea in urine. The synthetic urine had the following composition, per aqueous liter, and a pH of 6.69.

| | |
|---|---|
| Urea | 25 grams |
| NaCl | 9 grams |
| $MgSO_4 \cdot 5H_2O$ | 0.4 grams |
| $Ca(OAc)_2$ | 0.7 grams |
| $K_2SO_4$ | 4 grams |
| $(NH_4)_2SO_4$ | 2.5 grams |

Figure 2:
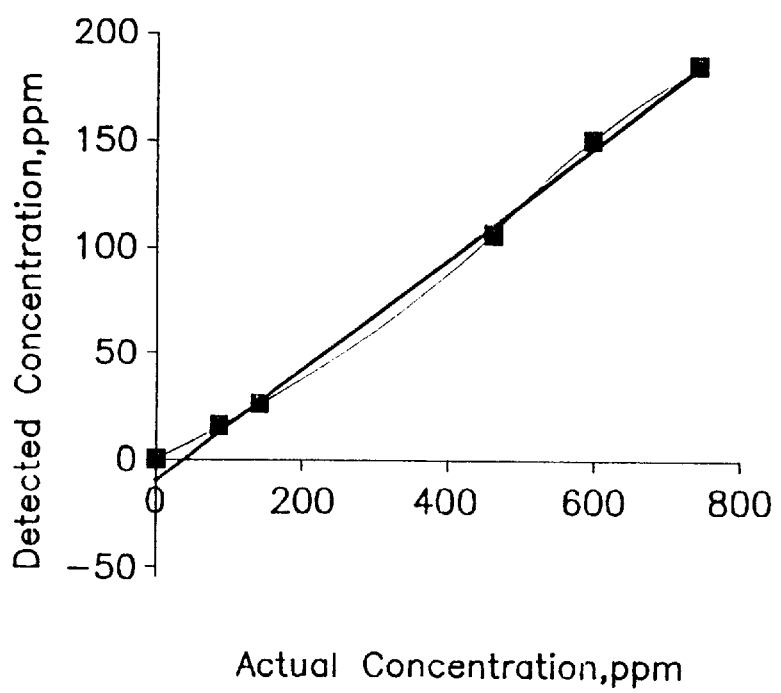
FIG. 2 illustrates a calibration curve used in Examples 1–6.

Prior to the synthetic urine insult, each fabric sample was placed in a 125 ml glass Erlenmeyer flask at 37° C. as shown in FIG. 1. Flask 1 was equipped with a 5 mm outer diameter glass tube 2, which extended into the flask through a Fisher brand twist-stop rubber stopper 3. Above the flask, a Fisher brand pure latex tubing 4 connected the glass tube 2 on one end, and a Drager ammonia diffusion tube 5 on the other end. The Drager tubes were identified as Drager 8101301. The ammonia diffusion tube 5 operates according to a color code, and changes to different colors depending on the ammonia concentration in its interior. Over time (i.e., at steady state), there is a linear correlation between the ammonia concentration inside the Drager tube 5 and the concentration inside the flask 1. This correlation is known from pre-established calibration tests, and is shown in FIG. 2. The calibration curve was generated using Drager tubes attached to flasks containing zero, 60, 150, 480, 600 and 750 ppm of ammonia, and from two ammonia calibration standard controls (60 ppm and 600 ppm ammonia). Referring to FIG. 2, the actual ammonia concentration inside the flask, and the detected concentration inside the Drager tube, are related according to the following equation:

Total NH$_3$ con., ppm =

$$\left[\frac{(\text{Drager tube reading/hours of exposure}) + 6.4092 \text{ ppm}}{0.2496}\right] - 25.68.$$

While the test for ammonia concentration holds some subjectivity, the trends observed below should hold if the tests are repeated. The six Examples evaluated for ammonia odor release/inhibition using synthetic urine, treated with bacteria were characterized as follows:

EXAMPLE 1

Only the 6 ml of synthetic urine, treated with the bacteria, was injected into the flask without a fabric sample.

EXAMPLE 2

A coform fabric sample was treated with 0.6% by weight AHCOVEL®Base N-62, a surfactant mixture of ethoxylated hydrogenated castor oil and sorbitan monooleate, supplied by Hodgson Chemical Co. The add-on percentage was calculated as follows:

$$\left(\frac{\text{Weight of wet fabric minus weight of dry fabric}}{\text{Weight of dry fabric}}\right) \times \% \text{ surfactant mixture in solution.}$$

The AHCOVEL®Base N-62 was applied to the fabric from an aqueous solution containing 0.30% by weight AHCOVEL®Base N-62.

EXAMPLE 3

A coform fabric sample was treated with 2.0% by weight Na$_2$EDTA (disodium EDTA) having the chemical formula C$_{10}$H$_{14}$N$_2$O$_8$Na$_2$·2H$_2$O, and 0.6% by weight AHCOVEL®Base N-62. The Na$_2$EDTA was supplied by Sigma Corp. The aqueous solution used for coating was prepared by mixing 1.0% by weight Na$_2$EDTA with water, and then adding 0.30% by weight AHCOVEL® to the solution.

EXAMPLE 4

A coform fabric sample was treated with 2.0% by weight Na$_x$LED3A from Hampshire Chemical Corp. and 0.6% by weight AHCOVEL®Base N-62. The aqueous solution used for coating was prepared by mixing 1.0% by weight Na$_x$LED3A with water, then adding just enough hydrochloric acid to reduce the pH to about 6.5 (which also reduced the surface tension of the solution). Then, 0.30% by weight AHCOVEL® was added to the mixture.

EXAMPLE 5

A coform fabric sample was treated with 2.1% by weight Na$_2$EDTA. The aqueous solution used for coating was prepared by mixing 1.0% Na$_2$EDTA and 0.5% by weight hexanol with water.

EXAMPLE 6

A coform fabric sample was treated with 2.1% by weight Na$_x$LED3A. The aqueous solution used for coating was prepared by mixing 1.0% Na$_x$LED3A with water, and adding just enough hydrochloric acid to reduce the pH to about 6.5 (thus reducing the surface tension of the solution).

Each Example was run in duplicate, with results reported as an average of duplicate samples. For each Example, the ammonia concentration was measured every hour for 10 hours. All of the fabric samples except Example 5 (treated with Na$_2$EDTA alone) had sufficient wettability to quickly absorb (within a few seconds) the insult of synthetic urine/bacteria. The fabric of Example 5 retained the urine insult on its outer surface for about 6–7 minutes before completely absorbing it. Nevertheless, it took about 5 hours for most of the Examples to produce enough ammonia to give reliable ammonia readings.

Figure 3:
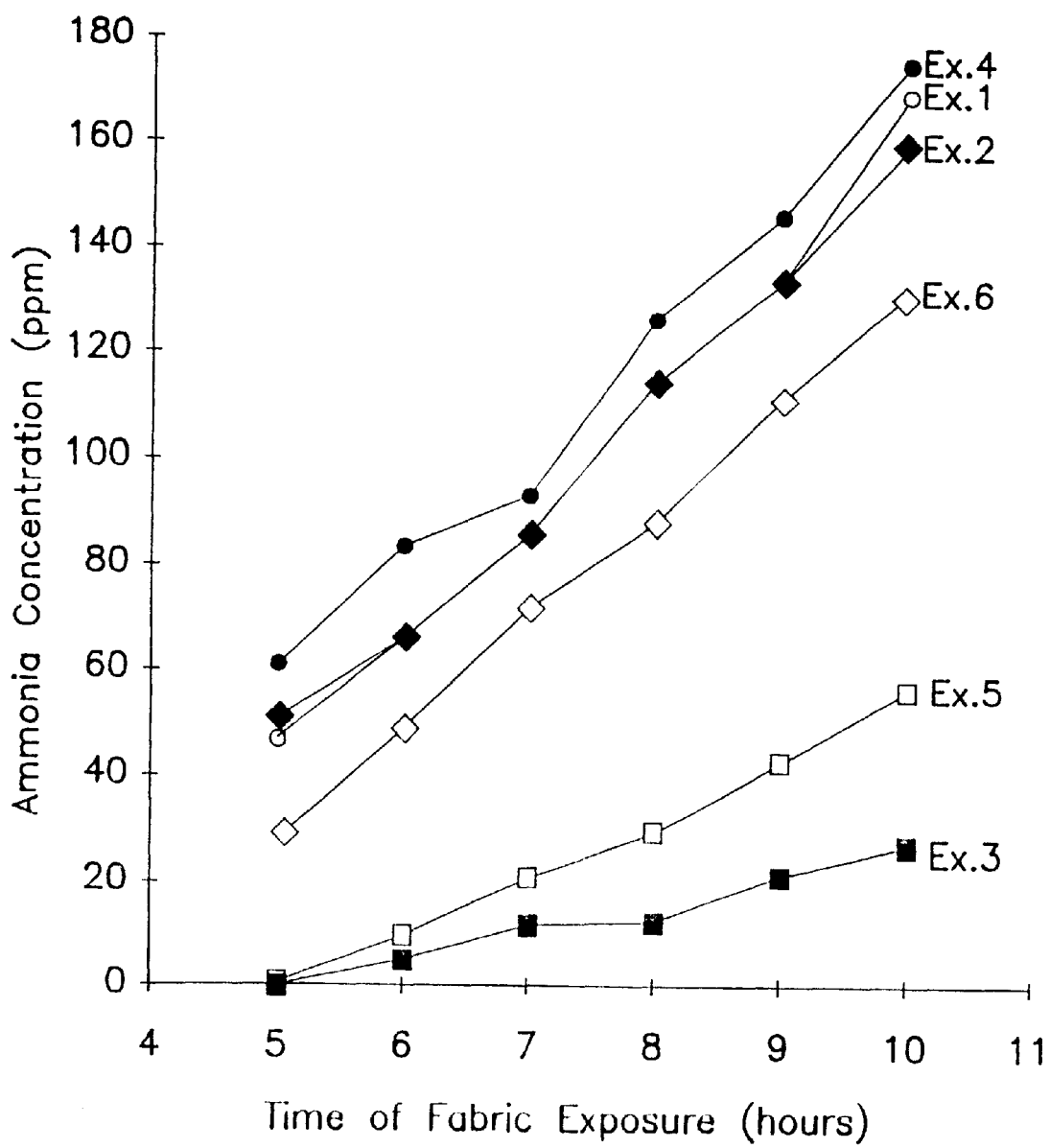
FIG. 3 is a plot showing ammonia concentration versus time, for Examples 1–6.

The actual ammonia concentrations in the flasks for periods between 5–10 hours are plotted in FIG. 3. The higher ammonia concentrations reflect lower inhibition of ammonia formation. The synthetic urine by itself (Example 1) and AHCOVEL® by itself (Example 2) exhibited no inhibition and high ammonia release levels. The combination of Na$_x$LED3A and AHCOVEL® (Example 4) also did not inhibit ammonia formation.

The combination of Na$_2$EDTA and AHCOVEL® (Example 3) showed the greatest inhibition of ammonia formation, as shown by the lowest release levels. The Na$_2$EDTA by itself (Example 5) inhibited ammonia formation, but did not exhibit adequate surface wetting, as indicated by the long time required for the synthetic urine/bacteria insult to enter the fabric. The Na$_x$LED3A by itself (Example 6) inhibited ammonia formation to some extent, and had adequate surface wetting.

Proteus mirabilis bacteria must be present in synthetic urine in order for ammonia to be found. Three additional Examples (not plotted) did not produce any ammonia. They were: a) an empty flask, b) synthetic urine without the bacteria, and c) coform fabric treated with 0.58% AHCOVEL®Base N-62 and exposed to synthetic urine without the bacteria.

EXAMPLES 7–12

(Odor Inhibition)

Essentially the same procedures described above for Examples 1–6 were used to measure odor inhibition of ammonia generated from human urine (pooled from three female donors). The same coform material and sample sizes were used. The fabric samples were treated with surface coatings using the same soaking, squeezing and drying procedures. The treated fabric samples were then each placed in a 125 ml glass Erlenmeyer flask at 37° C. as shown in FIG. 1, and were each exposed to an insult of 6 ml real urine at 37° C., which had been inoculated with 5.5×10$^9$ colony forming units/ml of proteus mirabilis bacteria and had a pH of 5.93.

The six Examples evaluated for ammonia odor release/inhibition using real urine, treated with the bacteria, were characterized as follows:

EXAMPLE 7

Only the 6 ml of real urine, treated with the bacteria, was injected into the flask without a fabric sample.

EXAMPLE 8

A coform fabric sample was treated with 0.6% by weight AHCOVEL®Base N-62, using the technique described for Example 2.

EXAMPLE 9

A coform fabric sample was treated with 2.0% by weight Na$_2$EDTA and 0.6% by weight AHCOVEL®Base N-62, using the technique described for Example 3.

EXAMPLE 10

A coform fabric sample was treated with 2.0% by weight $Na_xLED3A$ and 0.6% by weight AHCOVEL®Base N-62, using the technique described for Example 4.

EXAMPLE 11

A coform fabric sample was treated with 2.1% by weight $Na_2EDTA$, using the technique described for Example 5.

EXAMPLE 12

A coform fabric sample was treated with 2.1% by weight $Na_xLED3A$, using the technique described for Example 6.

Each Example was run in duplicate, with results reported as an average of duplicate samples. For each Example, the ammonia concentration was measured every hour for 10 hours. The total ammonia concentration was determined from a Drager tube using the calibration technique described above for Examples 1–6. In this instance, the calibration technique generated the following relationship.

Total $NH_3$ con., ppm =

$$\left[\frac{(\text{Drager tube reading/hours of exposure}) + 8.0032 \text{ ppm}}{0.2508}\right] - 31.91.$$

Figure 4:
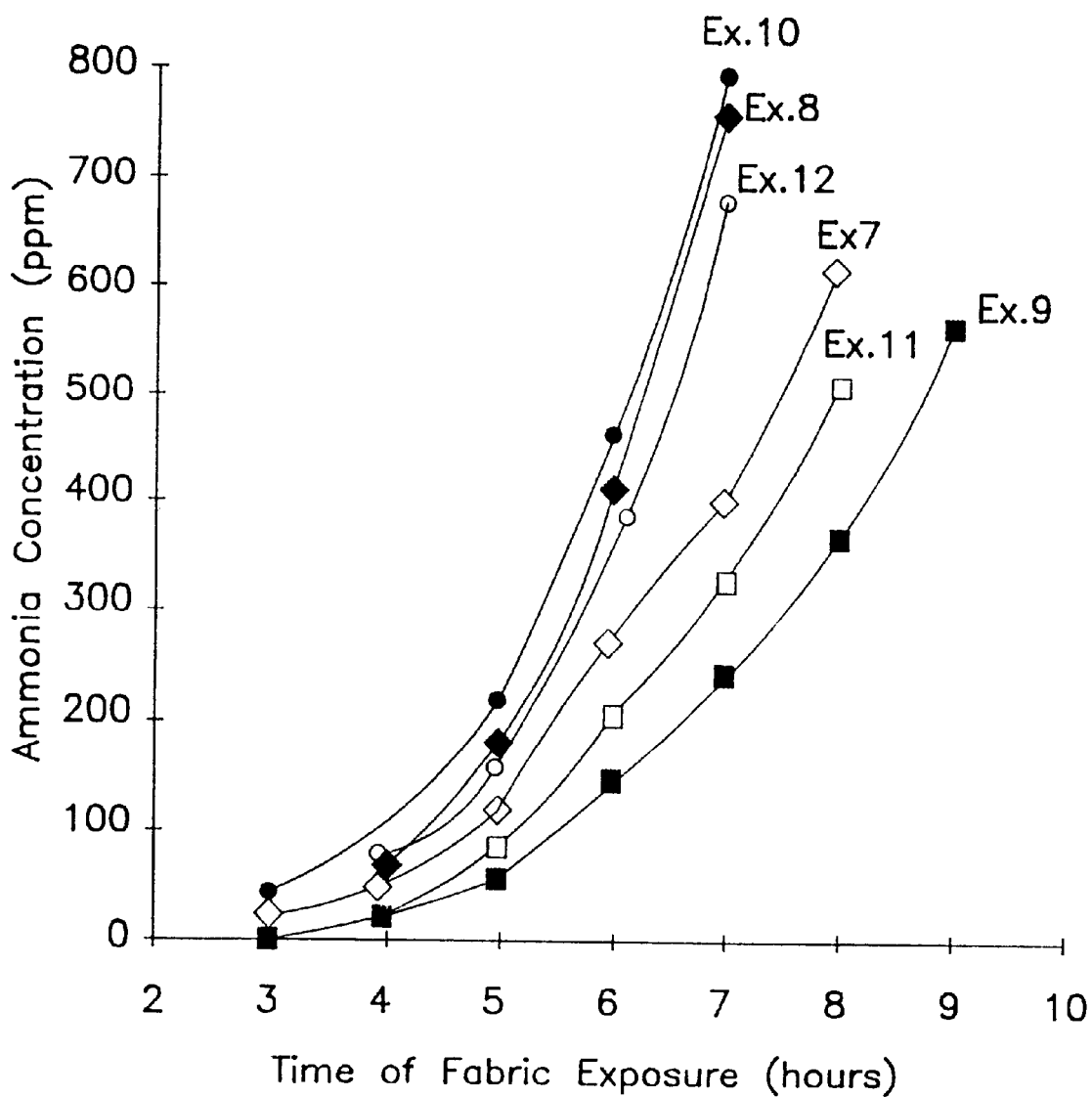
FIG. 4 is a plot showing ammonia concentration versus time, for Examples 7–12.

After 9 hours, all of the Examples had produced the maximum ammonia (1500 ppm) that could be measured by the Drager tube. All of the fabric samples except Example 11 (treated with $Na_2EDTA$ alone) had sufficient wettability to quickly absorb the insult of urine. The ammonia concentrations in the flasks, as measured hourly, are plotted in FIG. 4. Again, higher ammonia concentrations reflect lower inhibition of ammonia formation.

Of the six Examples exposed to human urine, only two of them showed odor inhibition compared to the control (Example 7) which did not utilize a fabric. The two Examples showing inhibition were the fabric treated with $Na_2EDTA$ and AHCOVEL®(Example 9) and the fabric treated with $Na_2EDTA$ alone (Example 11). Of the two, only the fabric of Example 9 exhibited adequate surface wetting.

Again, the proteus mirabilis bacteria must be present in human urine in order for ammonia to be found. Three additional Examples (not plotted) did not produce any ammonia. They were: a) an empty flask; b) human urine without the bacteria, and c) coforin treated with 0.6% AHCOVEL®Base N-62 and exposed to human urine without the bacteria.

EXAMPLES 13–17

(Odor Inhibition)

Similar procedures (to Examples 7–12) were used to measure odor inhibition generated from human urine in Examples 13–17. Examples 13–17 were designed to test odor inhibition of urine inoculated with a higher level, $7.4 \times 10^9$ colony forming units/ml, of proteus mirabilis bacteria, using higher levels of $Na_2EDTA$ in the surfactant-modified odor control agent. The same coforin material and sample sizes were used. The fabric samples were treated with the surfactant-modified odor control agents using the same soaking, squeezing and drying procedures. The treated fabric samples were then each placed in a 125-ml glass Erlenmeyer flask at 37° C. as shown in FIG. 1, and were each exposed to an insult of 6 ml of human urine at 37° C., which had been inoculated with the bacteria, and which had a pH of 5.96. For each Example, three fabric samples were treated, and the results were averaged.

The five Examples evaluated for ammonia odor release/inhibition in this set, were characterized as follows:

EXAMPLE 13

Only the 6 ml of real urine, treated with the higher amount of bacteria, was injected into the flask without a fabric sample.

EXAMPLE 14

A coform fabric sample was treated with 0.6% by weight AHCOVEL®Base N-62, using the technique described for Example 2.

EXAMPLE 15

A coform fabric sample was treated with 4.6% by weight $Na_2EDTA$ and 0.7% by weight AHCOVEL®Base N-62, using an aqueous solution similar to Example 3 except for higher concentrations.

EXAMPLE 16

A coform fabric sample was treated with 0.7% by weight CETIOL®81414E, an ethoxylated ester derivative of myristic acid, obtained from the Henkel Corporation. A technique similar to Example 2 was employed, except the CETIOL®was used instead of the AHCOVEL®.

EXAMPLE 17

A coform fabric sample was treated with 4.8% by weight $Na_2EDTA$ and 0.7% by weight CETIOL®81414E, using an aqueous solution similar to Example 15, except the CETIOL® was used instead of AHCOVEL®.

Figure 5:
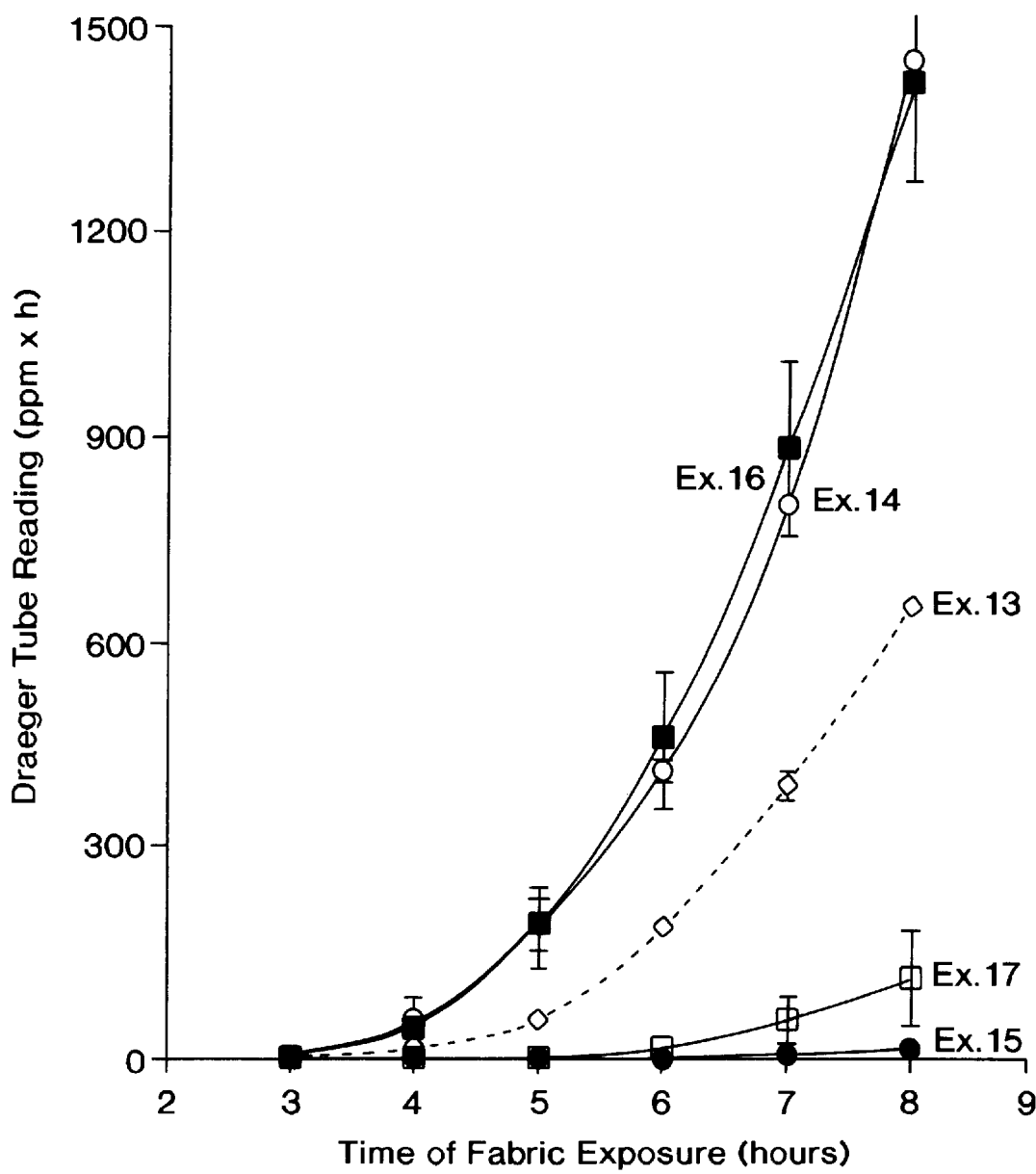
FIG. 5 is a plot showing ammonia Drager tube readings (representative of concentration) versus time, for Examples 13–17.

The Drager tube readings in the flasks for periods between 3–8 hours are plotted in FIG. 5. The higher Drager tube readings reflect lower inhibition of ammonia formation. The human urine by itself (Example 13) exhibited no odor inhibition and high ammonia release levels. The ammonia release levels were even higher for fabric samples treated with AHCOVEL® alone (Example 14) and with CETIOL® alone (Example 16). The fabrics treated with surfactant-modified odor control agents (Examples 15 and 17) showed substantial inhibition of ammonia formation, indicated by very low release levels. Of these, the samples treated with the $Na_2EDTA$/AHCOVEL® combination (Example 15) was somewhat more effective in inhibiting ammonia formation than the samples treated with the $Na_2EDTA$/CETIOL® combination (Example 17).

EXAMPLES 18–22

(Antimicrobial Behavior)

Samples (0.5 gram each) of coform fabric having a dry basis weight of 170 gsm and containing 30% by weight polypropylene meltblown fibers and 70% by weight pulp fibers, were exposed to an insult of 6 ml human urine at 37° C. The urine had been inoculated with $7.4 \times 10^9$ cfu/ml of proteus mirabilis bacteria. Prior to the urine insults, and procedures similar to those described in the preceding Examples, the coform samples were treated in aqueous solutions to yield the coatings described in Table 1, based on the dry weight of the coform. Following the urine insults, the samples were allowed to sit in the Erlenmeyer flasks as described above, at 37° C. for eight hours. After eight hours, the concentration of proteus mirabilis in the urine was measured, for each of the samples insulted with the urine. Table 1 reports the results of these measurements, reflecting an average of three samples for each Example:

TABLE 1

Proteus Mirabilis Populations After Eight Hours

| Example | Sample Characterization | Proteus Mirabilis Population, cfu/ml Urine After Eight Hours at 37° C. |
|---|---|---|
| 18 | Urine + 7.4 × 10$^9$ cfu/ml of proteus mirabilis | 5.4 × 10$^9$ |
| 19 | Coform treated with 0.6% by weight AHCOVEL ®Base N-62 and insulted with urine | 1.1 × 10$^9$ |
| 20 | Coform treated with 0.7% by weight CETIOL ®1414E and insulted with urine | 7.3 × 10$^8$ |
| 21 | Coform treated with 0.7% by weight AHCOVEL ® and 4.6% by weight Na$_2$EDTA | 3.4 × 10$^9$ |
| 22 | Coform treated with 0.7% by weight CETIOL ® and 4.8% by weight Na$_2$EDTA | 9.9 × 10$^8$ |

As shown in Examples 18–22, the surfactant-modified odor control agent did not result in lower concentrations of proteus mirabilis compared to the surfactant-only controls. Specifically, the fabric treated with AHCOVEL® and Na$_2$EDTA (Example 21) sustained a higher proteus mirabilis concentration than the fabric treated with only AHCOVEL® (Example 19). Similarly, the fabric treated with CETIOL® and Na$_2$EDTA (Example 22) sustained a higher proteus mirabilis concentration than the fabric treated with only CETIOL® (Example 20). Therefore, the inhibition of odor formation resulting from use of the surfactant-modified odor control agents, is not due to antimicrobial activity.

EXAMPLES 23–29

(Odor Inhibition)

The main purpose of these Examples was to compare the odor inhibition properties of surfactant-modified odor control agents formed by chemical reaction, with those formed by blending a surfactant with an odor control agent. Each Example represented an average performance of two 170 gsm coform samples (70% pulp fibers, 30% meltblown polypropylene) having weights of 0.5 gram. The surfactants, and surfactant-modified odor control agents, were applied by soaking the coform samples in aqueous solutions similar to those described in the preceding Examples, and the coform samples were dried using similar procedures. The samples were each exposed to an insult of 6 ml human urine, which had been inoculated with 8.6×10$^9$ cfu/ml of proteus mirabilis bacteria. The samples were each placed in an Erlenmeyer flask, and ammonia readings were recorded using a Drager tube using the procedures described above. Table 2 identifies each sample, and sets forth the Drager tube measurements (average of two samples for each Example) after two, four, five and six hours.

TABLE 2

Drager Tube Reading (ppm × hrs.) vs. Time

| Example | Sample Characterization | Drager Tube Readings and Standard Deviations | | | |
|---|---|---|---|---|---|
| | | 2 Hours | 4 Hours | 5 Hours | 6 Hours |
| 23 | Empty flask | 0 | 0 | 0 | 0 |
| 24 | Human Urine (no fabric, no bacterial inoculation) | 0 | 0 | 0 | 0 |
| 25 | Human Urine (no fabric, inoculated with proteus mirabilis) | 0 | 162 ± 18 | 450 ± 71 | 975 + 106 |
| 26 | Fabric treated with 0.6% AHCO-VEL ® Base N-62, insulted with inoculated human urine | 7.5 ± 3.5 | 400 ± 141 | 1100 ± 283 | ≧1500 |
| 27 | Fabric treated with 5.0% Na$_x$LED3A, insulted with inoculated human urine | 0 | 300 ± 141 | 800 ± 283 | ≧1500 |
| 28 | Fabric treated with 4.2% Na$_x$C8-ED3A, insulted with inoculated human urine | 0 | 325 ± 35 | 850 ± 71 | ≧1500 |
| 29 | Fabric treated with 3.8% Na$_2$EDTA and 0.6% AHCO-VEL ®, insulted with inoculated human urine | 0 | 50 ± 0 | 200 ± 0 | 525 ± 35 |

As shown above, fabrics treated with surfactant-modified odor control agents formed by chemical reaction (Examples 27 and 28) resulted in slightly lower Drager tube readings (slightly better odor control inhibition) than the fabric treated with surfactant alone (Example 26). However, the fabric treated with the surfactant-modified odor control agent formed by blending a surfactant and an odor control agent (Exhibit 29) exhibited by far the best odor inhibition. Two of the controls (Examples 23 and 24) confirm that no ammonia odor was detected in either an empty flask, or a flask containing urine that had not been inoculated with proteus mirabilis bacteria. Again, the formation of ammonia results from an interaction between proteus mirabilis, which is found on human skin, and urea which is found in urine.

EXAMPLES 30–44

(Odor Absorption)

Examples 30–44 tested the treated fabric samples for absorption of an existing odor, as opposed to inhibition of odor formation. The odor absorption test uses headspace gas chromatography (headspace GC) to measure the amount of an odorous compound that is removed form the gas phase by a treated fabric.

The headspace GC testing was conducted on a Hewlett-Packard HP5890 GC with a HP7694 Headspace Sampler (K-C RAST group). A J&W DB-624 (30 m length, 0.25 mm 1.D., 1.4 μm film) column and flame ionization detector (FID) were used. The column is relatively stable, and usually produces deviations in the range of 5–10% for replicate samples.

Two odorous compounds, triethylamine (TEA) and trimethylamine (TMA), were used in the headspace GC procedure. These compounds are both soluble in water and increase the pH (organic bases). They are suspected to cause odor in menstrual fluid.

The procedure involves placing a weighted piece of fabric (0.14 gram) inside a 20-cc headspace vial. Using a syringe, an aliquot of odor is also placed in the vial, taking care not to let the liquid and fabric come in contact. The vial is then sealed with a cap and septum and placed in the headspace GC oven at body temperature (37° C.). After 10 minutes, a syringe is inserted through the septum and into the vial to remove a 1-cc sample of the headspace (air inside the vial) which is then injected into the GC. This short exposure time of 10 minutes to the odor is kept constant for all fabrics. The GC is run isothermally at 100° C. for triethylamine (TEA) and at 110° C. for trimethylamine (TMA). The GC cycle time is 10 minutes.

The peak for TEA occurs between 5 and 5.5 minutes, and the peak for TMA occurs between 3 and 3.5 minutes. Initially, a standard vial with only the aliquot of odor (no fabric) is tested to define 0% odor absorption. To calculate the amount of headspace odor removed by a fabric, the peak area for TEA (or TMA) from the vial with fabric is compared to the peak area from this standard vial (no fabric). Testing is typically done with 2 μl of 99% pure TEA or 5 μl of 40% pure TMA and 0.14 grams of fabric. Results are presented as "% odor absorption" and as "mg odor absorbed/g fabric."

Fabric samples were tested in both the wet and dry state. It is expected that the fabric will exist somewhere in-between these two states in actual product use. For wet testing, the fabric was sealed and stored in the wet state immediately after treatment, or a dried treated fabric was dipped in distilled water and squeezed to remove excess liquid just prior to the headspace GC procedure. In this procedure, 0.14 g of the wet fabric was used. The wet fabric was tested and then allowed to dry. The fabric was then weighed again when dry to determine the amount of liquid that was present. The wet fabric samples contain different amounts of liquid so the odor absorption had to be normalized for the amount of wetness. This normalization must be done because it was found that the amount of liquid in a sample influences the amount of TEA that is absorbed. The following is a calculation that has been used to normalize odor absorption for wet samples.

Assume Fabric A has the following characteristics:
1. In the dry state, 0.14 g of Fabric A absorbs 5 mg TEA/g of dry fabric.
2. In the wet state, 0.14 g of Fabric A absorbs 10 mg TEA/g of wet fabric.
3. The wet Fabric A is allowed to dry and is re-weighed. The dried weight is found to be 0.056 g. A calculation is done using this dried weight and gives 25 mg TEA absorbed/g of dried fabric.
4. The "% Wetness" for the wet state of Fabric A is calculated with the following equation:

$$\frac{\text{weight of wet fabric} - \text{weight of dried fabric}}{\text{weight of dried fabric}} \times 100\% = \% \text{ Wetness}$$

Using the above equation with 0.14 g for the wet fabric and 0.056 g for the dried fabric, "150% Wetness" is calculated for the wet state of Fabric A.

5. A "Wetness Factor" is then calculated by taking the "% Wetness" for the wet state of Fabric A and dividing it by 100% Wetness. This gives a "Wetness Factor" of 1.5 for the wet state of Fabric A (150% Wetness divided by 100% Wetness).
6. Finally, the "mg TEA absorbed/g of dried fabric" for the wet state of Fabric A is divided by the "Wetness Factor" of 1.5:

$$\frac{25 \text{ mg TEA/a dried fabric}}{1.5 \text{ (Wetness Factor)}} = 16.7 \text{ mg TEA/g of "dry" fabric}$$

All of the TEA and TMA data for fabrics in the wet state expressed as "mg odor/g of dry fabric" have been normalized in this fashion.

Replicates (typically duplicates) of each fabric were run using the headspace GC procedure. Since the fabric samples were typically exposed to the odor for a constant time of only 10 minutes, odor absorption properties are most likely being compared in a kinetic regime instead of under equilibrium conditions. To ensure that time of odor exposure is kept constant for fabrics, care must be taken to place the aliquot of odor in the vial just before the vial is placed in the oven. Some fabric samples were also exposed to the odor for a longer time (e.g., over night) to obtain equilibrium absorption values, but these values are probably not indicative of the conditions experienced by fabrics in actual use. It is believed that odor absorption should occur rapidly, certainly before the product user is able to detect the odor.

Examples 30–44 were run using 170 gsm coform fabrics (30% by weight meltblown polypropylene fibers, 70% by weight staple-length pulp fibers). The coform fabric samples were treated with the disodium salt form of EDTA ($Na_2EDTA \cdot 2H_2O$) and with the combination of $Na_2EDTA \cdot 2H_2O$ and surfactant (AHCOVEL®Base N-62 or CETIOL®81414E). Hexanol had to be used in the treatment solution that contained only $Na_2EDTA \cdot 2H_2O$ to lower the surface tension and thus facilitate the application of $Na_2EDTA$ to the coform. Recall from the above Odor Inhibition data that the $Na_2EDTA$+AHCOVEL®and $Na_2EDTA$+CETIOL® treatments provided coform with improved inhibition properties to ammonia and with better fluid handling properties, compared to fabric treated with only $Na_2EDTA$. These treatments were also compared in triethylamine (TEA) absorption studies using the headspace GC technique (described above). Table 3 shows the data. Also, FIG. 6 displays a plot of the amount (%) of headspace TEA absorbed by the fabrics treated with Na₂EDTA, AHCOVEL®, and Na₂EDTA+AHCOVEL®.

TABLE 3

TEA Absorption Of Treated Coform Samples

| Example | Dry Samples | % TEA Absorbed | mg TEA Absorbed/ g Wet Fabric | mg TEA Absorbed/ g Dry Fabric |
|---|---|---|---|---|
| 30 | Untreated Coform | 14.2 ± 1.0 | N/A | 1.48 ± 0.11 |
| 31 | 0.7% AHCOVEL | 30.4 ± 7.0 | N/A | 3.16 ± 0.72 |
| 32 | 0.7% CETIOL | 33.5 ± 3.2 | N/A | 3.49 ± 0.33 |
| 33 | 2.4% Na₂EDTA/ (Hexanol Wetting Agent) | 44.6 ± 6.4 | N/A | 4.64 ± 0.66 |
| 34 | 2.3% Na₂EDTA/ 0.7% AHCOVEL | 47.3 ± 4.5 | N/A | 4.91 ± 0.48 |
| 35 | 3.8% Na₂EDTA/ 0.6% AHCOVEL | 57.9 ± 4.5 | N/A | 6.00 ± 0.47 |
| 36 | 4.9% Na₂EDTA/ 0.7% AHCOVEL | 74.5 ± 3.0 | N/A | 7.78 ± 0.33 |
| 37 | 4.9% Na₂EDTA/ 0.7% AHCOVEL (overnight) | 90.9 ± 0.3 | N/A | 9.43 ± 0.02 |
| 38 | 5.4% Na₂EDTA/ 0.8% CETIOL | 70.8 ± 0.5 | N/A | 7.38 ± 0.00 |
| | Wet Samples | | | |
| 39 | Untreated Coform | 30.5 ± 1.8 | 3.20 ± 0.19 | 4.11 ± 0.07 |
| 40 | 0.6% AHCOVEL | 32.7 ± 1.0 | 3.40 ± 0.11 | 8.41 ± 0.17 |
| 41 | 0.6% CETIOL | 35.3 ± 3.0 | 3.70 ± 0.30 | 5.98 ± 0.06 |
| 42 | 3.8% Na₂EDTA/ 0.6% AHCOVEL | 49.3 ± 1.7 | 5.13 ± 0.16 | 7.89 ± 0.01 |
| 43 | 4.9% Na₂EDTA/ 0.7% AHCOVEL | 69.6 ± 0.2 | 7.21 ± 0.07 | 10.42 ± 0.15 |
| 44 | 5.4% Na₂EDTA/ 0.8% CETIOL | 52.4 | 5.41 | 7.91 |

Figure 6:
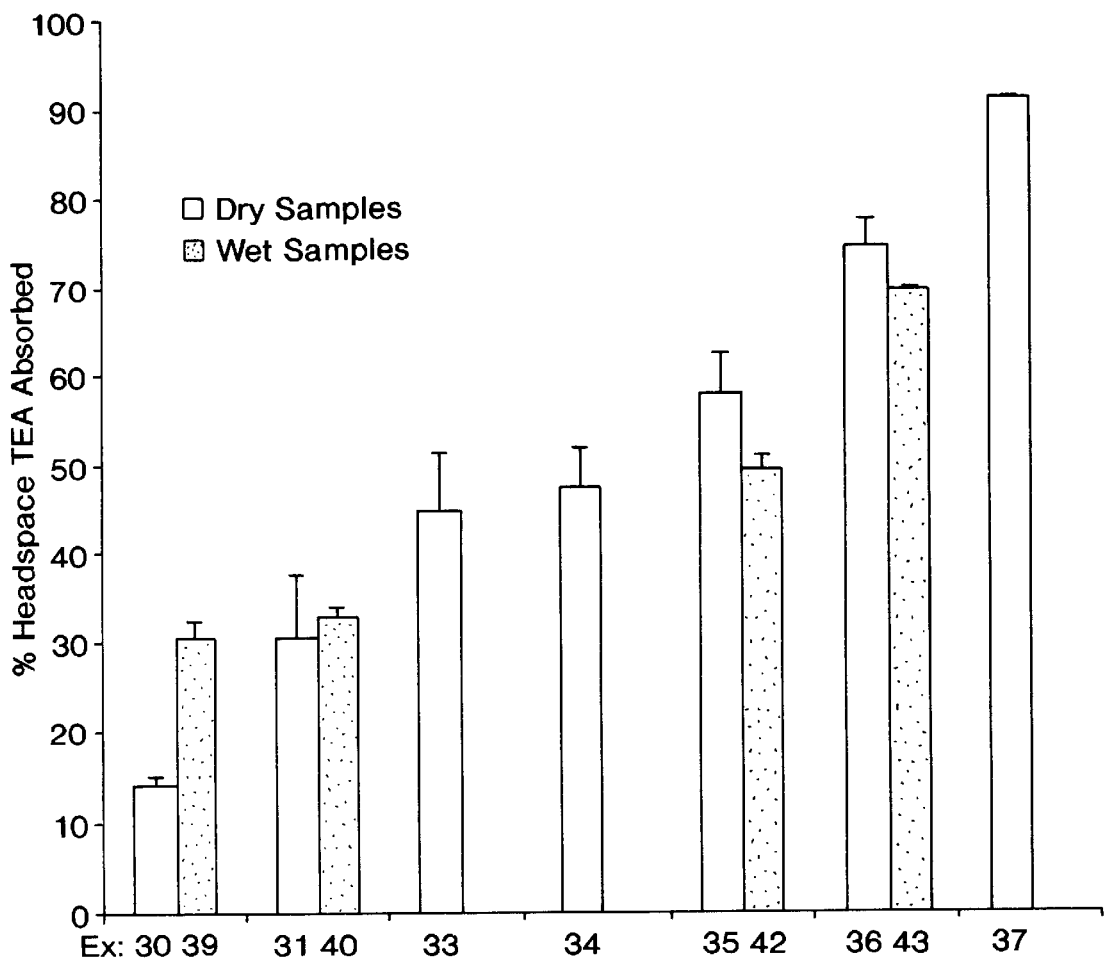
FIG. 6 is a bar graph showing triethylamine (TEA) absorption for most of Examples 30–44.

The data in Table 3 and FIG. 6 illustrate that TEA absorption (based on dry fabric weight) follows the same trend for fabrics in the dry and wet states. Therefore, the wet state does not adversely affect TEA absorption properties for any of the fabrics.

The AHCOVEL®treatment (0.6–0.7% by weight) increased TEA absorption by a factor of two for both the dry and wet states (Examples 31 and 40), compared to untreated coform fabrics (Examples 30 and 39). The CETIOL®treatment (0.6–0.7% by weight) increased TEA absorption by a factor of two for treated fabric in the dry state (Example 32) and, to a lesser extent in the wet state (Example 41), compared to untreated coform fabric (Examples 30 and 39).

Dry coform treated with 2.4% Na₂EDTA (Example 33) provided the same TEA absorption as fabric treated with both Na₂EDTA (2.3% add-on) and AHCOVEL® (0.7% add-on) (Example 34). The Na2EDTA treatment and Na₂EDTA +AHCOVEL® treatment produced 50% more TEA absorption compared to coform 15 treated with only 0.7 wt % AHCOVEL® (Example 31).

In both dry and wet states, as the level of Na₂EDTA was increased for coform treated with Na₂EDTA+AHCOVEL®, the amount of TEA absorption also increased (Examples 34–36 and 42–43).

The Na₂EDTA+CETIOL®-treated coform (Example 3 8) and Na₂EDTA +AHCOVEL®-treated coform (Example 36) absorbed similar amounts of TEA in the dry state. In the wet state, coform treated with Na₂EDTA+AHCOVEL® (Example 43) was better than coform treated with Na₂EDTA+CETIOL® (Example 44).

As the time of exposure to TEA was increased from 10 minutes to overnight, the amount of TEA absorption increased from 74% to 91% for coform treated with 4.9% Na₂EDTA+0.7% AHCOVEL® (Examples 36 and 37).

It is obvious from the TEA data for coform treated with disodium EDTA chelating agent or surfactant (AHCOVEL® or CETIOL®)+ disodium EDTA (Table 14 and FIG. 6) that the chelating agent alone provides as much TEA absorption as the combination of chelating agent+ surfactant. Thus, in terms of TEA odor absorption, there is not any benefit in including AHCOVEL® or CETIOL® as part of the EDTA treatment for coform fabric. However, as shown in previous Examples, inhibition properties to ammonia formation and fluid handling properties were not as good for coform treated with only EDTA. Indeed, the combination of EDTA and surfactant (AHCOVEL® or CETIOL®) improved the odor inhibition.

EXAMPLES 45–64

(Odor Absorption)

The primary purpose of Examples 45–64 was to compare the TEA odor absorption using the different salt forms of EDTA (namely, Na₂EDTA, Na₃EDTA and Na₄EDTA). Treated fabric samples were prepared by soaking fabric samples in aqueous treatment solutions (as described in previous Examples) and allowing them to dry, or leaving them in the wet state. For Examples 45–54, the 170 gsm coform fabric (70% by weight pulp fibers, 30% by weight polypropylene meltblown fibers) was used. For Examples 55–64, a 50 gsm airlaid fabric was used. The airlaid fabric contained 85% by weight pulp fibers, 11.2% by weight bicomponent staple (polyester core/polyethylene sheath) fibers and 3.8% by weight latex adhesive.

To make the surfactant-modified odor control agents, each EDTA salt was mixed with water and AHCOVEL® Base N-62 surfactant. The surfactant lowered the surface tension of the solution, and was necessary in order to wet out and effectively treat the coform fabrics. Also, the fluid handling properties of the fabrics would be compromised if the surfactant were not used.

The fabric samples were tested for odor absorption using the procedure described above, for Examples 30–44. Table 4 shows the data obtained using coform fabric examples. Table 5 shows the data obtained using airlaid fabric samples.

TABLE 4

TEA Absorption Of Treated Coform Samples

| Example | Dry Samples | % TEA Absorbed | mg TEA Absorbed/ g Wet Fabric | mg TEA Absorbed/ g Dry Fabric |
|---|---|---|---|---|
| 45 | Untreated Coform | 14.2 ± 1.0 | N/A | 1.48 ± 0.11 |
| 46 | 0.7% AHCOVEL | 30.4 ± 7.0 | N/A | 3.16 ± 0.72 |
|    | 3.8% Na₂EDTA/ 0.6% AHCOVEL | 57.9 ± 4.5 | N/A | 6.00 ± 0.47 |
| 48 | 4.7% Na₃EDTA/ 0.8% AHCOVEL | 24.0 ± 1.9 | N/A | 2.50 ± 0.17 |
| 49 | 5.2% Na₄EDTA/ 0.7% AHCOVEL | 13.9 ± 0.0 | N/A | 1.44 ± 0.01 |
| | Wet Samples | | | |
| 50 | Untreated Coform | 30.5± 1.8 | 3.20 ± 0.19 | 4.11 ± 0.07 |
| 51 | 0.6% AHCOVEL | 32.7± 1.0 | 3.40 ± 0.11 | 8.41 ± 0.17 |
| 52 | 3.8% Na₂EDTA/ 0.6% AHCOVEL | 49.3 ± 1.7 | 5.13 ± 0.16 | 7.89 ± 0.01 |

TABLE 4-continued

TEA Absorption Of Treated Coform Samples

| Example | Dry Samples | % TEA Absorbed | mg TEA Absorbed/ g Wet Fabric | mg TEA Absorbed/ g Dry Fabric |
|---|---|---|---|---|
| 53 | 4.5% Na$_3$EDTA/ 0.7% AHCOVEL | 42.5 ± 0.6 | 4.43 ± 0.06 | 8.62 ± 0.28 |
| 54 | 4.9% Na$_4$EDTA/ 0.6% AHCOVEL | 40.4 ± 2.8 | 4.23 ± 0.30 | 7.82 ± 1.22 |

TABLE 5

TEA Absorption Of Treated Airlaid Samples

| Example | Dry Samples | % TEA Absorbed | mg TEA Absorbed/ g Wet Fabric | mg TEA Absorbed/ g Dry Fabric |
|---|---|---|---|---|
| 55 | "as received" airlaid | 12.0 ± 0.6 | N/A | 1.25 ± 0.06 |
| 56 | 0.6% AHCOVEL | 29.4 ± 4.0 | N/A | 3.07 ± 0.42 |
| 57 | 3.5% Na$_2$EDTA/ 0.6% AHCOVEL | 43.3 ± 4.4 | N/A | 4.18 ± 0.01 |
| 58 | 4.0% Na$_3$EDTA/ 0.7% AHCOVEL | 20.1 ± 2.6 | N/A | 2.09 ± 0.26 |
| 59 | 5.2% Na$_4$EDTA/ 0.7% AHCOVEL | 12.9 ± 0.5 | N/A | 1.35 ± 0.04 |
| | Wet Samples | | | |
| 60 | "as received" airlaid | 31.1 ± 0.5 | 3.23 ± 0.03 | 3.94 ± 0.02 |
| 61 | 0.6% AHCOVEL | 32.9 ± 4.1 | 3.43 ± 0.20 | 6.49 ± 0.35 |
| 62 | 3.5% Na$_2$EDTA/ 0.6% AHCOVEL | 44.9 ± 0.5 | 4.68 ± 0.05 | 7.74 ± 0.40 |
| 63 | 4.1% Na$_3$EDTA/ 0.7% AHCOVEL | 45.4 ± 6.0 | 4.73 ± 0.62 | 7.74 ± 1.80 |
| 64 | 4.7% Na$_4$EDTA/ 0.6% AHCOVEL | 50.3 ± 5.0 | 5.27 ± 0.55 | 9.15 ± 0.81 |

The data in Tables 4 and 5 illustrate that for both coform and airlaid fabrics in the dry state, TEA absorption was the best for fabrics treated with surfactant-modified odor control agents combining the lower salt form of EDTA with AHCOVEL®Base N-62. The TEA absorption becomes progressively lower for the higher salt forms of EDTA, such that the combination of Na$_3$EDTA with AHCOVEL® performed similarly to AHCOVEL® alone.

For both coform and airlaid fabrics in the wet state, TEA absorption remained high, and was fairly consistent for both the lower and higher salt forms of EDTA combined with AHCOVEL®. Apparently, the presence of water either masked or offset any negative absorption effects caused by the higher salt forms of EDTA.

EXAMPLES 65–84

(Odor Absorption)

The primary purpose of Examples 65–84 was to compare the TEA odor absorption for other surfactant-modified odor control agents; including Na$_x$LED3A, Na$_x$C$_8$ED3A, and a combination of sodium gluconate and AHCOVEL® Base N-62; with that resulting from the use of AHCOVEL® Base N-62 alone. Again, the fabrics were treated with aqueous solutions of the surfactant-modified odor control agents, using techniques similar to those described in previous Examples. The treated fabric samples were tested for odor absorption using the techniques described for Examples 30–44. Table 6 shows the data obtained using the 170 gsm coform of Examples 45–54 as the fabric. Table 7 shows the data obtained using the 50 gsm airlaid fabric of Examples 55–64, as the fabric.

TABLE 6

TEA Absorption Of Treated Coform Fabrics

| Example | Dry Samples | % TEA Absorbed | mg TEA Absorbed/ g Wet Fabric | mg TEA Absorbed/ g Dry Fabric |
|---|---|---|---|---|
| 65 | Untreated Coform | 14.2 ± 1.0 | N/A | 1.48 ± 0.11 |
| 66 | 0.7% AHCOVEL | 30.4 ± 7.0 | N/A | 3.16 ± 0.72 |
| 67 | 5.1% Na$_x$LED3A | 36.7 ± 1.3 | N/A | 3.82 ± 0.11 |
| 68 | 4.9% Na$_x$C$_8$-ED3A | 38.1 ± 4.0 | N/A | 3.97 ± 0.42 |
| 69 | 4.9% Sodium Gluconate/0.6% AHCOVEL | 22.6 ± 0.3 | N/A | 2.35 ± 0.03 |
| | Wet Samples | | | |
| 70 | Untreated Coform | 30.5 ± 1.8 | 3.20 ± 0.19 | 4.11 ± 0.07 |
| 71 | 0.6% AHCOVEL | 32.7 ± 1.0 | 3.40 ± 0.11 | 8.41 ± 0.17 |
| 72 | 5.2% Na$_x$LED3A | 46.9 ± 4.5 | 4.88 ± 0.46 | 9.15 ± 1.76 |
| 73 | 4.0% Na$_x$C$_8$-ED3A | 51.5 ± 0.4 | 5.37 ± 0.02 | 9.60 ± 1.02 |
| 74 | 5.0% Sodium Gluconate/0.6% AHCOVEL | 33.4 ± 0.5 | 3.49 ± 0.04 | 5.94 ± 0.33 |

TABLE 7

TEA Absorption Of Treated Airlaid Fabrics

| Example | Dry Samples | % TEA Absorbed | mg TEA Absorbed/ g Wet Fabric | mg TEA Absorbed/ g Dry Fabric |
|---|---|---|---|---|
| 75 | "as received" airlaid | 12.0 ± .6 | N/A | 1.25 ± 0.06 |
| 76 | 0.60% AHCOVEL | 29.4 ± 4.0 | N/A | 3.07 ± 0.42 |
| 77 | 4.0% Na$_x$LED3A | 62.2 ± 26.7 | N/A | 6.48 ± 2.81 |
| 78 | 4.4% Na$_x$C$_8$-ED3A | 58.9 ± 17.0 | N/A | 6.12 ± 1.76 |
| 79 | 4.7% Sodium Gluconate/0.6% AHCOVEL | 21.5 ± 0.4 | N/A | 2.23 ± 0.04 |
| | Wet Samples | | | |
| 80 | "as received" airlaid | 31.1 ± 0.5 | 3.23 ± 0.03 | 3.94 ± 0.02 |
| 81 | 0.6% AHCOVEL | 32.9 ± 4.1 | 3.43 ± 0.20 | 6.49 ± 0.35 |
| 82 | 4.7% Na$_x$LED3A | 44.4 ± 5.7 | 4.66 ± 0.60 | 8.35 ± 0.22 |
| 83 | 4.2% Na$_x$C$_8$-ED3A | 54.7 ± 0.5 | 5.71 ± 0.08 | 9.23 ± 0.25 |
| 84 | 4.9% Sodium Gluconate/0.6% AHCOVEL | 30.5 ± 4.6 | 3.18 ± 0.46 | 4.87 ± 0.86 |

The chelating surfactant treatments (Na$_x$LED3A and Na$_x$C$_8$ED3A) caused improved TEA absorption for the airlaid fabric samples, but not as much for the coform fabric samples. However, the combination of sodium gluconate and AHCOVEL®Base N-62 did not cause improved odor absorption.

EXAMPLES 85–88

(Odor Absorption)

The primary purpose of Examples 85–88 was to select some of the best fabric samples based on the foregoing TEA absorption results and test them for absorption of trimethylamine (TMA). Fabrics similar to those evaluated in Examples 36 and 38, combining high levels of $Na_2EDTA$ with either AHCOVEL® Base N-62 or CETIOL® 1414E, were selected for these tests. Table 8 shows the absorption results for TMA, using 170 gsm coform fabric samples (70% by weight pulp fibers, 30% by weight polypropylene meltblown fibers).

TABLE 8

TMA Absorption Of Treated Coform Samples

| Example | Samples | Dry State | | Wet State | |
| --- | --- | --- | --- | --- | --- |
| | | mg of TEA Absorbed/ g of Dry Fabric | % TEA Absorbed | mg of TMA Absorbed/ g of Dry Fabric | % TMA Absorbed |
| 85 | Untreated 170 gsm Coform | 0.32 ± 0.17 | 3.6 ± 1.9 | 5.28 ± 0.09 | 48.3 ± 0.1 |
| 86 | 0.6% AHCOVEL | 1.17 ± 0.28 | 13.0 ± 3.1 | 6.69 ± 0.47 | 55.4 ± 1.2 |
| 87 | 4.7% $Na_2EDTA$/ 0.7% AHCOVEL | 8.83 ± 0.04 | 97.1 ± 0.5 | 9.04 ± 0.48 | 69.9 ± 0.6 |
| 88 | 5.4% $Na_2EDTA$/ 0.8% CETIOL | 8.65 ± 0.15 | 95.6 ± 1.7 | 10.14 ± 0.34 | 74.9 ± 1.6 |

As shown in Table 10, the surfactant-modified odor control agents were very effective in absorbing TMA, in both the dry and wet states. The inventive fabrics of Examples 87 and 88 showed considerably greater TMA absorption than untreated fabrics (Example 85), and fabrics treated only with AHCOVEL®Base N-62 (Example 86).

While the embodiments of the invention described herein are presently preferred, various modifications and improvements can be made without departing from the spirit and scope of the invention. The scope of the invention is indicated by the appended claims, and all changes that fall within the meaning and range of equivalents are intended to be embraced therein.

We claim:

1. A treated thermoplastic layer material comprising a thermoplastic substrate layer treated with a surfactant-modified odor control agent selected from the group consisting of a) a blend of a surfactant with an odor control chelating agent, b) a reaction product of a surfactant-producing compound with an odor control chelating agent, and c) combinations of the foregoing;

wherein the odor control chelating agent comprises a compound selected from ethylenediamine tetraacetic acid, the sodium salts of ethylenediamine tetraacetic acid, and combinations thereof; and wherein the surfactant-producing compound comprises an ethoxylated ester derivative of myristic acid.

2. The treated, thermoplastic layer material of claim 1, wherein the substrate comprises a thermoplastic nonwoven filament web.

3. The treated, thermoplastic layer material of claim 1, wherein the substrate comprises a thermoplastic film.

4. The treated, thermoplastic layer material of claim 1, wherein the substrate comprises a thermoplastic foam layer.

5. The treated, thermoplastic layer material of claim 1, wherein the substrate comprises a porous, water permeable layer material.

6. The treated, thermoplastic layer material of claim 1, wherein the substrate comprises a mixture of nonwoven filaments and pulp fibers.

7. The treated, thermoplastic layer material of claim 1, wherein the substrate comprises an air laid web.

8. A treated thermoplastic layer material comprising a thermoplastic substrate layer treated with a surfactant-modified odor control agent produced by chemically reacting a surfactant-producing compound with an odor control chelating agent;

wherein the odor control chelating agent comprises a compound selected from ethylenediamine tetraacetic acid, the sodium salts of ethylenediamine tetraacetic acid, and combinations thereof; and wherein the surfactant-producing compound comprises a mixture of ethoxylated hydrogenated castor oil and sorbitan monooleate.

9. The treated, thermoplastic layer material of claim 8, wherein the substrate comprises a thermoplastic nonwoven filament web.

10. The treated, thermoplastic layer material of claim 8, wherein the substrate comprises a thermoplastic film.

11. The treated, thermoplastic layer material of claim 8, wherein the substrate comprises a thermoplastic foam layer.

12. The treated, thermoplastic layer material of claim 8, wherein the substrate comprises a porous, water permeable layer material.

13. The treated, thermoplastic layer material of claim 8, wherein the substrate comprises a mixture of nonwoven filaments and pulp fibers.

14. The treated, thermoplastic layer material of claim 8, wherein the substrate comprises an air laid web.

15. A treated thermoplastic layer material comprising a thermoplastic substrate layer treated with a surfactant-modified odor control agent selected from the group consisting of a) a blend of a surfactant with an odor control chelating agent, b) a reaction product of a surfactant-producing compound with an odor control chelating agent, and c) combinations of the foregoing;

wherein the surfactant-modified odor control agent comprises a sodium salt of lauroyl ethylenediamine triacetic acid.

16. The treated, thermoplastic layer material of claim 15, wherein the substrate comprises a thermoplastic nonwoven filament web.

17. The treated, thermoplastic layer material of claim 15, wherein the substrate comprises a thermoplastic film.

18. The treated, thermoplastic layer material of claim 15, wherein the substrate comprises a thermoplastic foam layer.

19. The treated, thermoplastic layer material of claim 15, wherein the substrate comprises a porous, water permeable layer material.

20. The treated, thermoplastic layer material of claim 15, wherein the substrate comprises a mixture of nonwoven filaments and pulp fibers.

21. The treated, thermoplastic layer material of claim 15, wherein the substrate comprises an air laid web.

22. A treated thermoplastic layer material comprising a thermoplastic substrate layer treated with a surfactant-modified odor control agent selected from the group consisting of a) a blend of a surfactant with an odor control chelating agent, b) a reaction product of a surfactant-producing compound with an odor control chelating agent, and c) combinations of the foregoing;
wherein the surfactant-modified odor control agent comprises a sodium salt of capryloyl ethylenediamine triacetic acid.

23. The treated, thermoplastic layer material of claim 22, wherein the substrate comprises a thermoplastic nonwoven filament web.

24. The treated, thermoplastic layer material of claim 22, wherein the substrate comprises a thermoplastic film.

25. The treated, thermoplastic layer material of claim 22, wherein the substrate comprises a thermoplastic foam layer.

26. The treated, thermoplastic layer material of claim 22, wherein the substrate comprises a porous, water permeable layer material.

27. The treated, thermoplastic layer material of claim 22, wherein the substrate comprises a mixture of nonwoven filaments and pulp fibers.

28. The treated, thermoplastic layer material of claim 22, wherein the substrate comprises an air laid web.

29. A treated thermoplastic layer material comprising a thermoplastic nonwoven filament web treated with a surfactant-modified chelating agent, produced by chemically reacting a surfactant-producing compound with an odor control chelating agent;
the treated nonwoven web having better wettability and odor control than the nonwoven web without the surfactant-modified chelating agent;
wherein the odor comprises a malodor selected from ammonia, trimethylamine, triethylamine, isovaleric acid, dimethyldisulfide, dimethyltrisulfide, indole, skatole, and combinations thereof;
wherein the surfactant-modified odor control agent comprises a reaction product of a polyaminocarboxylic acid or alkali metal salt thereof, with an alkyl compound.

30. A treated thermoplastic layer material comprising a thermoplastic nonwoven filament web treated with a surfactant-modified chelating agent, produced by chemically reacting a surfactant-producing compound with an odor control chelating agent;
the treated nonwoven web having better wettability and odor control than the nonwoven web without the surfactant-modified chelating agent;
wherein the odor comprises a malodor selected from ammonia, trimethylamine, triethylamine, isovaleric acid, dimethyldisulfide, dimethyltrisulfide, indole, skatole, and combinations thereof;
wherein the surfactant-modified odor control agent comprises a reaction product of a polyaminocarboxylic acid or alkali metal salt thereof, with an acyl compound.

31. A treated thermoplastic layer material comprising a thermoplastic nonwoven filament web treated with a surfactant-modified chelating agent;
the treated nonwoven web having better wettability and odor control than the nonwoven web without the surfactant-modified chelating agent;
wherein the odor comprises a malodor selected from ammonia, trimethylamine, triethylamine, isovaleric acid, dimethyldisulfide, dimethyltrisulfide, indole, skatole, and combinations thereof; and
wherein the surfactant-modified odor control agent comprises a sodium salt of lauroyl ethylenediamine triacetate.

32. A treated thermoplastic layer material comprising a thermoplastic nonwoven filament web treated with a surfactant-modified chelating agent;
the treated nonwoven web having better wettability and odor control than the nonwoven web without the surfactant-modified chelating agent;
wherein the odor comprises a malodor selected from ammonia, trimethylamine, triethylamine, isovaleric acid, dimethyldisulfide, dimethyltrisulfide, indole, skatole, and combinations thereof; and
wherein the surfactant-modified odor control agent comprises a sodium salt of capryloyl ethylenediamine triacetic acid.

33. A treated thermoplastic layer material comprising a thermoplastic nonwoven filament web treated with a surfactant-modified chelating agent, produced by chemically reacting a surfactant-producing compound with an odor control chelating agent;
the treated nonwoven web having better wettability and odor control than the nonwoven web without the surfactant-modified chelating agent;
wherein the odor comprises a malodor selected from ammonia, trimethylamine, triethylamine, isovaleric acid, dimethyldisulfide, dimethyltrisulfide, indole, skatole, and combinations thereof;
wherein the surfactant-modified odor control agent comprises a salt of ethylenediamine tetraacetic acid, ethoxylated hydrogenated castor oil, and sorbitan monooleate.

34. A treated thermoplastic layer material comprising a thermoplastic nonwoven filament web treated with a surfactant-modified chelating agent;
the treated nonwoven web having better wettability and odor control than the nonwoven web without the surfactant-modified chelating agent;
wherein the odor comprises a malodor selected from ammonia, trimethylamine, triethylamine, isovaleric acid, dimethyldisulfide, dimethyltrisulfide, indole, skatole, and combinations thereof;
wherein the surfactant-modified odor control agent comprises a salt of ethylenediamine tetraacetic acid and an ethoxylated ester derivative of myristic acid.

* * * * *